US010131887B2

(12) United States Patent
Reichert et al.

(10) Patent No.: US 10,131,887 B2
(45) Date of Patent: *Nov. 20, 2018

(54) DNA POLYMERASES WITH INCREASED 3'-MISMATCH DISCRIMINATION

(71) Applicant: Roche Molecular Systems, Inc., Pleasanton, CA (US)

(72) Inventors: Fred Reichert, San Leandro, CA (US); Keith Bauer, San Rafael, CA (US); Thomas W. Myers, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/805,479

(22) Filed: Nov. 7, 2017

(65) Prior Publication Data

US 2018/0119117 A1  May 3, 2018

Related U.S. Application Data

(60) Continuation of application No. 15/138,029, filed on Apr. 25, 2016, now Pat. No. 9,840,698, which is a division of application No. 14/278,720, filed on May 15, 2014, now Pat. No. 9,340,827, which is a division of application No. 13/162,694, filed on Jun. 17, 2011, now Pat. No. 8,759,062.

(60) Provisional application No. 61/356,219, filed on Jun. 18, 2010.

(51) Int. Cl.
*C12N 9/12* (2006.01)
*C12Q 1/6806* (2018.01)

(52) U.S. Cl.
CPC ......... *C12N 9/1252* (2013.01); *C12Q 1/6806* (2013.01); *C12Y 207/07007* (2013.01)

(58) Field of Classification Search
None
See application file for complete search history.

(56) References Cited

U.S. PATENT DOCUMENTS

2009/0148891 A1   6/2009  Bauer et al.
2011/0318786 A1  12/2011  Reichert et al.

FOREIGN PATENT DOCUMENTS

WO     08/034110 A2   3/2008
WO     08/046612 A1   4/2008

OTHER PUBLICATIONS

Exner, Thomas E.; "Insights into the high fidelity of a DNA polymerase I mutant"; 2009, Journal of Molecular Modeling, vol. 15, No. 10, pp. 1271-1280.
Guo et al., "Protein Tolerance to Random Amino Acid Change", Proceedings of the National Academy of Sciences of the United States of America, vol. 101(25), Jun. 2004, pp. 9205-9210.
Kermekchiev, Miko B. et al.; "Mutants of Taq DNA polymerase resistant to PCR inhibitors allow DNA amplification from whole blood and crude soil samples"; 2009, Nucleic Acids Research, vol. 37, No. 5, pp. 1-14.
Kranaster, Ramon et al.; "One-step RNA pathogen detection with reverse transcriptase activity of a mutated thermostable Thermus aquaticus DNA"; 2010, Biotechnol., J., vol. 5, pp. 224-231.
Ngo et al., The Protein Folding Problem and Tertiary Structure Prediction, 1994, 433 and 492-495.
Ong, Jennifer L. et al.; "Directed Evolution of DNA Polymerase, RNA Polymerase and Reverse Transcriptase Activity in a Single Polypeptide"; 2006, J. Mol. Biol., vol. 361, pp. 537-550.
Patel et al.; "Prokaryotic DNA Polymerase I: Evolution, Structure, and "Base Flipping" Mechanism for Nucleotide Selection"; 2001, J. Mol. Biol., vol. 308, pp. 823-837.
Sauter, Katherina B.M. et al.; "Evolving Thermostable Reverse Transcriptase Activity in a DNA Polymerase Scaffold"; 2006, Angew. Chem. Int. Ed., vol. 45, pp. 7633-7635.
Vichier-Guerre, Sophie et al.; "A Population of Thermostable Reverse Transcriptases Evolved from Thermus aquaticus DNA Polymerase I by Phage Display"; 2006, Angew. Chem. Int. Ed., vol. 45, pp. 6133-6137.
Database UniProt [Online]; Oct. 14, 2008 (Oct. 14, 2008), "SubName: Full=DNA polymerase I: EC=2.7.7.7; "XP000002658109, retrived from EBI accession No. UNIPROT: B5EQI8 Database accession No. B5EQI8.
Database UniProt [Online]; Jun. 12, 2007 (Jun. 12, 2007), "SubName: Full=DNA polymerase I: EC=2.7.7.7; "XP000002658120, retrived from EBI accession No. UNIPROT: A5FYN0 Database accession No. A5FYN0.
NCBI Reference Sequence: YP_002221092.1, DNA Polymerase I [Acidthiobacillus ferrooxidans ATCC 53993] (2010).
NCBI Reference Sequence: NP_274975.1, DNA polymerase I [Neisseria meningitidis MC58] (2010).
GenBank: EDR36726.1, DNA Polymerase I [Coxiella burnetti RA 334] (2008).

*Primary Examiner* — Richard G Hutson
(74) *Attorney, Agent, or Firm* — Kilpatrick Townsend and Stockton LLP

(57) ABSTRACT

Disclosed are mutant DNA polymerases having increased 3'-mismatch discrimination relative to a corresponding, unmodified polymerase. The mutant polymerases are useful in a variety of disclosed primer extension methods. Also disclosed are related compositions, including recombinant nucleic acids, vectors, and host cells, which are useful, e.g., for production of the mutant DNA polymerases.

20 Claims, 2 Drawing Sheets

Specification includes a Sequence Listing.

*Figure 1*

```
                                          *
Z05     AWIEKTLEEGRKRGYVE TLF G RR R Y V PDLNARVK  (SEQ ID NO:12)
Taq     AWIEKTLEEGRRRGYVE TLF G RR R Y V PDLEARVK  (SEQ ID NO:13)
Tfi     AWIAKTLEEGRKKGYVE TLF G RR R Y V PDLNARVK  (SEQ ID NO:14)
Tfl     AWIEGTLEEGRRRGYVE TLF G RR R Y V PDLNARVK  (SEQ ID NO:15)
Sps17   AWIAKTLEEGRKKGYVE TLF G RR R Y V PDLNARVK  (SEQ ID NO:16)
Tth     AWIEKTLEEGRKRGYVE TLF G RR R Y V PDLNARVK  (SEQ ID NO:17)
Tca     AWIEKTLEEGRKRGYVE TLF G RR R Y V PDLNARVK  (SEQ ID NO:18)
Tma     DYIQRVVSEAKEKGYVR TLF G RK R D I PQLMARDR  (SEQ ID NO:19)
Tne     SYIQQVVAEAKEKGYVR TLF G RK R D I PQLMARDK  (SEQ ID NO:20)
Taf     EYLKRMKDEARKKGYVT TLF G RR R Y I PQLRSKNG  (SEQ ID NO:21)
Dra     RYINHTLDFGRTHGYVE TLY G RR R Y V PGLSSRNR  (SEQ ID NO:23)
Bst     QYMDNIVQEAKQKGYVT TLL H RR R Y L PDITSRNF  (SEQ ID NO:24)
Bca     RYMENIVQEAKQKGYVT TLL H RR R Y L PDITSRNF  (SEQ ID NO:25)
        -------------GYVX₁TLX₂X₃RX₄X₅X₆X₇P-------  (SEQ ID NO:26)
```

FIGURE 2

| A. | Sequence identities over the entire polymerase I enzyme (corresponding to amino acids 1-834 of Z05) | | | | | | | | | | | | |
|---|---|---|---|---|---|---|---|---|---|---|---|---|---|
| Name | Z05 | Taq | Tfi | Tfl | Sps17 | Tth | Tca | Dra | Tma | Tne | Taf | Bst | Bca |
| Z05 |  | 0.864 | 0.833 | 0.859 | 0.839 | 0.962 | 0.958 | 0.459 | 0.374 | 0.368 | 0.359 | 0.407 | 0.408 |
| Taq | 0.864 |  | 0.831 | 0.854 | 0.836 | 0.872 | 0.864 | 0.468 | 0.382 | 0.368 | 0.351 | 0.397 | 0.397 |
| Tfi | 0.833 | 0.831 |  | 0.82 | 0.991 | 0.829 | 0.824 | 0.45 | 0.371 | 0.375 | 0.353 | 0.405 | 0.397 |
| Tfl | 0.859 | 0.854 | 0.82 |  | 0.824 | 0.853 | 0.848 | 0.462 | 0.381 | 0.374 | 0.356 | 0.397 | 0.398 |
| Sps17 | 0.839 | 0.836 | 0.991 | 0.824 |  | 0.835 | 0.83 | 0.452 | 0.375 | 0.377 | 0.355 | 0.407 | 0.399 |
| Tth | 0.962 | 0.872 | 0.829 | 0.853 | 0.835 |  | 0.989 | 0.463 | 0.373 | 0.367 | 0.358 | 0.406 | 0.406 |
| Tca | 0.958 | 0.864 | 0.824 | 0.848 | 0.83 | 0.989 |  | 0.46 | 0.371 | 0.365 | 0.356 | 0.404 | 0.404 |
| Dra | 0.459 | 0.468 | 0.45 | 0.462 | 0.452 | 0.463 | 0.46 |  | 0.334 | 0.325 | 0.314 | 0.338 | 0.339 |
| Tma | 0.374 | 0.382 | 0.371 | 0.381 | 0.375 | 0.373 | 0.371 | 0.334 |  | 0.854 | 0.567 | 0.37 | 0.377 |
| Tne | 0.368 | 0.368 | 0.375 | 0.374 | 0.377 | 0.367 | 0.365 | 0.325 | 0.854 |  | 0.558 | 0.377 | 0.376 |
| Taf | 0.359 | 0.351 | 0.353 | 0.356 | 0.355 | 0.358 | 0.356 | 0.314 | 0.567 | 0.558 |  | 0.356 | 0.364 |
| Bst | 0.407 | 0.397 | 0.405 | 0.397 | 0.407 | 0.406 | 0.404 | 0.338 | 0.37 | 0.377 | 0.356 |  | 0.881 |
| Bca | 0.408 | 0.397 | 0.397 | 0.398 | 0.399 | 0.406 | 0.404 | 0.339 | 0.377 | 0.376 | 0.364 | 0.881 |  |

| B. | Sequence identities over polymerase sub domain only (corresponding to amino acids 420-834 of Z05) | | | | | | | | | | | | |
|---|---|---|---|---|---|---|---|---|---|---|---|---|---|
| Name | Z05 | Taq | Tfi | Tfl | Sps17 | Tth | Tca | Dra | Tma | Tne | Taf | Bst | Bca |
| Z05 |  | 0.901 | 0.845 | 0.891 | 0.845 | 0.975 | 0.973 | 0.563 | 0.483 | 0.478 | 0.44 | 0.498 | 0.49 |
| Taq | 0.901 |  | 0.879 | 0.901 | 0.877 | 0.906 | 0.901 | 0.561 | 0.488 | 0.473 | 0.44 | 0.503 | 0.495 |
| Tfi | 0.845 | 0.879 |  | 0.857 | 0.997 | 0.853 | 0.853 | 0.566 | 0.495 | 0.49 | 0.449 | 0.512 | 0.49 |
| Tfl | 0.891 | 0.901 | 0.857 |  | 0.855 | 0.889 | 0.889 | 0.571 | 0.492 | 0.48 | 0.444 | 0.494 | 0.485 |
| Sps17 | 0.845 | 0.877 | 0.997 | 0.855 |  | 0.853 | 0.853 | 0.566 | 0.495 | 0.49 | 0.449 | 0.512 | 0.49 |
| Tth | 0.975 | 0.906 | 0.853 | 0.889 | 0.853 |  | 0.99 | 0.563 | 0.478 | 0.473 | 0.437 | 0.496 | 0.488 |
| Tca | 0.973 | 0.901 | 0.853 | 0.889 | 0.853 | 0.99 |  | 0.563 | 0.478 | 0.473 | 0.437 | 0.496 | 0.488 |
| Dra | 0.563 | 0.561 | 0.566 | 0.571 | 0.566 | 0.563 | 0.563 |  | 0.45 | 0.448 | 0.426 | 0.474 | 0.454 |
| Tma | 0.483 | 0.488 | 0.495 | 0.492 | 0.495 | 0.478 | 0.478 | 0.45 |  | 0.883 | 0.622 | 0.474 | 0.475 |
| Tne | 0.478 | 0.473 | 0.49 | 0.48 | 0.49 | 0.473 | 0.473 | 0.448 | 0.883 |  | 0.615 | 0.476 | 0.473 |
| Taf | 0.44 | 0.44 | 0.449 | 0.444 | 0.449 | 0.437 | 0.437 | 0.426 | 0.622 | 0.615 |  | 0.46 | 0.473 |
| Bst | 0.498 | 0.503 | 0.512 | 0.494 | 0.512 | 0.496 | 0.496 | 0.474 | 0.474 | 0.476 | 0.46 |  | 0.898 |
| Bca | 0.49 | 0.495 | 0.49 | 0.485 | 0.49 | 0.488 | 0.488 | 0.454 | 0.475 | 0.473 | 0.473 | 0.898 |  |

US 10,131,887 B2

DNA POLYMERASES WITH INCREASED 3'-MISMATCH DISCRIMINATION

CROSS-REFERENCE TO RELATED PATENT APPLICATIONS

The present application is a continuation of U.S. patent application Ser. No. 15/138,029, filed Apr. 25, 2016, now U.S. Pat. No. 9,840,698, which is a divisional of U.S. patent application Ser. No. 14/278,720, filed May 15, 2014, now U.S. Pat. No. 9,340,827, which is a divisional of U.S. patent application Ser. No. 13/162,694, filed Jun. 17, 2011, now U.S. Pat. No. 8,759,062, which claims benefit of priority to U.S. Provisional Patent Application No. 61/356,219, filed Jun. 18, 2010, each of which is incorporated by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 088883-1065876_seq_1st.TXT, created on Oct. 26, 2017, 122,474 bytes, machine format IBM-PC, MS-Windows operating system, is hereby incorporated by reference in its entirety for all purposes.

FIELD OF THE INVENTION

The present invention provides DNA polymerases with increased 3'-mismatch discrimination and their use in various applications, including nucleic acid polynucleotide extension and amplification.

BACKGROUND OF THE INVENTION

DNA polymerases are responsible for the replication and maintenance of the genome, a role that is central to accurately transmitting genetic information from generation to generation. DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. In vivo, DNA polymerases participate in a spectrum of DNA synthetic processes including DNA replication, DNA repair, recombination, and gene amplification. During each DNA synthetic process, the DNA template is copied once or at most a few times to produce identical replicas. In contrast, in vitro, DNA replication can be repeated many times such as, for example, during polymerase chain reaction (see, e.g., U.S. Pat. No. 4,683,202).

In the initial studies with polymerase chain reaction (PCR), the DNA polymerase was added at the start of each round of DNA replication (see U.S. Pat. No. 4,683,202, supra). Subsequently, it was determined that thermostable DNA polymerases could be obtained from bacteria that grow at elevated temperatures, and that these enzymes need to be added only once (see U.S. Pat. No. 4,889,818 to Gelfand and U.S. Pat. No. 4,965,188 to Mullis). At the elevated temperatures used during PCR, these enzymes are not irreversibly inactivated. As a result, one can carry out repetitive cycles of polymerase chain reactions without adding fresh enzymes at the start of each synthetic addition process. DNA polymerases, particularly thermostable polymerases, are the key to a large number of techniques in recombinant DNA studies and in medical diagnosis of disease. For diagnostic applications in particular, a target nucleic acid sequence may be only a small portion of the DNA or RNA in question, so it may be difficult to detect the presence of a target nucleic acid sequence without amplification.

The overall folding pattern of DNA polymerases resembles the human right hand and contains three distinct subdomains of palm, fingers, and thumb. (See Beese et al., *Science* 260:352-355, 1993); Patel et al., *Biochemistry* 34:5351-5363, 1995). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a mean deviation of about one Å amongst mammalian pol α and prokaryotic pol I family DNA polymerases (Wang et al., *Cell* 89:1087-1099, 1997). Motif A begins structurally at an antiparallel β-strand containing predominantly hydrophobic residues and continues to an α-helix. The primary amino acid sequence of DNA polymerase active sites is exceptionally conserved. In the case of motif A, for example, the sequence DYSQIELR (SEQ ID NO:28) is retained in polymerases from organisms separated by many millions years of evolution, including, e.g., *Thermus aquaticus, Chlamydia trachomatis*, and *Escherichia coli*.

In addition to being well-conserved, the active site of DNA polymerases has also been shown to be relatively mutable, capable of accommodating certain amino acid substitutions without reducing DNA polymerase activity significantly. (See, e.g., U.S. Pat. No. 6,602,695) Such mutant DNA polymerases can offer various selective advantages in, e.g., diagnostic and research applications comprising nucleic acid synthesis reactions. Thus, there is a need in the art for identification of amino acid positions amenable to mutation to yield improved polymerase activities. The present invention, as set forth herein, meets these and other needs.

BRIEF SUMMARY OF THE INVENTION

Provided herein are DNA polymerases having increased 3'-mismatch discrimination relative to a corresponding, unmodified control polymerase, and methods of making and using such DNA polymerases. In some embodiments, the polymerase is a thermostable DNA polymerase. In some embodiments, the DNA polymerase is a thermoactive DNA polymerase. In some embodiments, the DNA polymerase is derived from a *Thermus* species. In some embodiments, the DNA polymerase is derived from a *Thermotoga* species. In some embodiments, the amino acid of the DNA polymerase corresponding to position 730 of SEQ ID NO:1 is any amino acid other than R, and the control DNA polymerase has the same amino acid sequence as the DNA polymerase except that the amino acid of the control DNA polymerase corresponding to position 730 of SEQ ID NO:1 is R. For example, in some embodiments, the amino acid at the position corresponding to position 730 of SEQ ID NO:1 is selected from G, A, V, L, I, M, F, W, P, S, T, C, Y, N, Q, D, E, K, or H. In some embodiments, the amino acid at the position corresponding to position 730 of SEQ ID NO:1 is A, C, D, G, or N.

In some embodiments, the amino acid at the position corresponding to position 730 of SEQ ID NO:1 is an amino acid having a nonpolar, uncharged side-chain (e.g., G, A, L, M, W, P, F, C, V, or I). In some embodiments, the amino acid at the position corresponding to position 730 of SEQ ID NO:1 is an amino acid having a polar, uncharged side-chain (e.g., N, Q, H, S, T, or Y). In some embodiments, the amino acid at the position corresponding to position 730 of SEQ ID NO:1 is an amino acid having a polar, negatively-charged side-chain (e.g., D or E).

In some embodiments, the DNA polymerase having increased 3'-mismatch discrimination comprises a motif in the polymerase domain comprising G-Y-V-$X_1$-T-L-$X_2$-$X_3$-R-$X_4$-$X_5$-$X_6$-$X_7$-P, wherein:
$X_1$ is E, R or T;
$X_2$ is F, Y or L;
$X_3$ is G or H;
$X_4$ is R or K;
$X_5$ is any amino acid other than R;
$X_6$ is Y or D; and
$X_7$ is V, I or L (SEQ ID NO:8).

In some embodiments, the DNA polymerase having increased 3'-mismatch discrimination comprises a motif in the polymerase domain comprising G-Y-V-$X_1$-T-L-F-G-R-$X_4$-$X_5$-$X_6$-$X_7$-P, wherein:
$X_1$ is E or R;
$X_4$ is R or K;
$X_5$ is any amino acid other than R;
$X_6$ is Y or D; and
$X_7$ is V or I (SEQ ID NO:9).

In some embodiments, the DNA polymerase having increased 3'-mismatch discrimination comprises a motif in the polymerase domain comprising G-Y-V-E-T-L-F-G-R-R-$X_5$-Y-V-P, wherein:
$X_5$ is any amino acid other than R (SEQ ID NO:10).

In some embodiments, $X_5$ is an amino acid having a nonpolar, uncharged side-chain (e.g., G, A, L, M, W, P, F, C, V, or I), a polar, uncharged side-chain (e.g., N, Q, H, S, T, or Y) or a polar, negatively-charged side-chain (e.g., D or E).

In some embodiments, $X_5$ is A, C, D, G, or N (SEQ ID NO:11).

In some embodiments, the amino acid of the DNA polymerase corresponding to position 580 of SEQ ID NO:1 is any amino acid other than D or E. In some embodiments, the amino acid of the DNA polymerase corresponding to position 580 of SEQ ID NO:1 is any amino acid other than D. In some embodiments, the amino acid of the DNA polymerase corresponding to position 580 of SEQ ID NO:1 is selected from the group consisting of L, G, T, Q, A, S, N, R and K. In some embodiments, the amino acid of the DNA polymerase corresponding to position 580 of SEQ ID NO:1 is G.

Various DNA polymerases are amenable to mutation according to the present invention. Particularly suitable are thermostable polymerases, including wild-type or naturally occurring thermostable polymerases from various species of thermophilic bacteria, as well as synthetic thermostable polymerases derived from such wild-type or naturally occurring enzymes by amino acid substitution, insertion, or deletion, or other modification. Exemplary unmodified forms of polymerase include, e.g., CS5 (SEQ ID NO:29), CS6 (SEQ ID NO:30) or Z05 DNA polymerase (SEQ ID NO:1), or a functional DNA polymerase having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto. Other unmodified polymerases include, e.g., DNA polymerases from any of the following species of thermophilic bacteria (or a functional DNA polymerase having at least 80%, 81%, 82%, 83%, 84%, 85%, 86%, 87%, 88%, 89%, 90%, 91%, 92%, 93%, 94%, 95%, 96%, 97%, 98% or 99% sequence identity to such a polymerase): *Thermotoga maritima* (SEQ ID NO:38); *Thermus aquaticus* (SEQ ID NO:2); *Thermus thermophilus* (SEQ ID NO:6); *Thermus flavus* (SEQ ID NO:4); *Thermus filiformis* (SEQ ID NO:3); *Thermus* sp. Sps17 (SEQ ID NO:5); *Thermus* sp. Z05 (SEQ ID NO:1); *Thermotoga neopolitana* (SEQ ID NO:39); *Thermosipho africanus* (SEQ ID NO:37); *Thermus caldophilus* (SEQ ID NO:7), *Deinococcus radiodurans* (SEQ ID NO:36), *Bacillus stearothermophilus* (SEQ ID NO:40) or *Bacillus caldotenax* (SEQ ID NO:41). Suitable polymerases also include those having reverse transcriptase (RT) activity and/or the ability to incorporate unconventional nucleotides, such as ribonucleotides or other 2'-modified nucleotides.

While thermostable DNA polymerases possessing efficient 3'-mismatch discrimination activity are particularly suited for performing PCR, thermoactive, but not thermostable DNA polymerases possessing efficient 3'-mismatch discrimination activity also are amenable to mutation according to the present invention.

In some embodiments, the DNA polymerase is a *Thermus* DNA polymerase. For example, in some embodiments, the DNA polymerase has at least 80%, 81%, 82%, 83%, 84%, 85%, 86%, 87%, 88%, 89%, 90%, 91%, 92%, 93%, 94%, 95%, 96%, 97%, 98%, 99% sequence identity to a polymerase selected from the group consisting of:
(a) a *Thermus* sp. Z05 DNA polymerase (Z05) (SEQ ID NO:1);
(b) a *Thermus aquaticus* DNA polymerase (Taq) (SEQ ID NO:2);
(c) a *Thermus filiformis* DNA polymerase (Tfi) (SEQ ID NO:3);
(d) a *Thermus flavus* DNA polymerase (Tfl) (SEQ ID NO:4);
(e) a *Thermus* sp. Sps17 DNA polymerase (Sps17) (SEQ ID NO:5);
(f) a *Thermus thermophilus* DNA polymerase (Tth) (SEQ ID NO:6); and
(g) a *Thermus caldophilus* DNA polymerase (Tca) (SEQ ID NO:7).

In some embodiments, the DNA polymerase is a *Thermotoga* DNA polymerase. For example, in some embodiments, the DNA polymerase has at least 80%, 81%, 82%, 83%, 84%, 85%, 86%, 87%, 88%, 89%, 90%, 91%, 92%, 93%, 94%, 95%, 96%, 97%, 98%, 99% sequence identity to a polymerase selected from the group consisting of:
(a) a *Thermotoga maritima* DNA polymerase (Tma) (SEQ ID NO:38);
(b) a *Thermotoga neopolitana* DNA polymerase (Tne) (SEQ ID NO:39);

In some embodiments, the DNA polymerase has at least 80%, 81%, 82%, 83%, 84%, 85%, 86%, 8'7%, 88%, 89%, 90%, 91%, 92%, 93%, 94%, 95%, 96%, 97%, 98%, 99% sequence identity to SEQ ID NO:1. In some embodiments, the DNA polymerase is a *Thermus* sp. Z05 DNA polymerase (Z05) DNA polymerase (i.e., SEQ ID NO:1), except that the amino acid at position 730 is any amino acid other than R. For example, in some embodiments, the amino acid at the position corresponding to position 730 of SEQ ID NO:1 is selected from G, A, V, L, I, M, F, W, P, S, T, C, Y, N, Q, D, E, K, or H. In some embodiments, the DNA polymerase is a Z05 DNA polymerase, and the amino acid at position 730 is A, C, D, G, or N. In some embodiments, the DNA polymerase is a Z05 DNA polymerase further comprising a substitution at position 580, and the amino acid at position 580 is any amino acid other than D or E. In some embodiments, the DNA polymerase is a Z05 DNA polymerase, and the amino acid at position 580 is any amino acid other than D. In some embodiments, the DNA polymerase is a Z05 DNA polymerase, and the amino acid at position 580 is selected from the group consisting of L, G, T, Q, A, S, N, R and K. In some embodiments, the DNA polymerase is a Z05 DNA polymerase, and the amino acid at position 580 is G.

The mutant or improved polymerase can include other, non-substitutional modifications. One such modification is a thermally reversible covalent modification that inactivates the enzyme, but which is reversed to activate the enzyme upon incubation at an elevated temperature, such as a temperature typically used for polynucleotide extension. Exemplary reagents for such thermally reversible modifications are described in U.S. Pat. Nos. 5,773,258 and 5,677, 152 to Birch et al., which are expressly incorporated by reference herein in their entirety.

In some embodiments, the 3'-mismatch activity is determined using a mutant BRAF V600R target polynucleotide having the nucleic acid sequence of SEQ ID NO:35 (wild type BRAF=SEQ ID NO:34) in the presence of a forward primer that is perfectly matched to the mutant sequence and has a single 3' A:C mismatch to the wild type sequence in one or more reaction mixtures having a predetermined number of copies of wild-type BRAF V600 target polynucleotide and a predetermined number of copies of mutant BRAF V600R target polynucleotide equal in number or fewer than the number of copies of wild-type target (e.g., 10,000 or fewer copies). Two or more reaction mixtures can have titrated numbers of copies of mutant BRAF V600R target polynucleotide (e.g., 1:5 titrations, 1:10 titrations, e.g., 10,000 copies, 1000 copies, 100 copies, 10 copies, 1 copy, 0 copies in several reaction mixtures). The 3'-mismatch discrimination ability of a polymerase of the invention can be compared to the 3'-mismatch discrimination ability of a reference polymerase (e.g., a naturally occurring or unmodified polymerase), over a preselected unit of time, as described herein. Polymerases with increased 3'-mismatch discrimination ability will not amplify the wild-type sequence when contacted with a primer that is perfectly matched to a mutant allele, or will require a greater number of PCR cycles to amplify the wild-type sequence using the mutant allele-specific primer (i.e., exhibit a higher Cp value), in comparison to a naturally occurring or unmodified polymerase.

In various other aspects, the present invention provides a recombinant nucleic acid encoding a mutant or improved DNA polymerase as described herein, a vector comprising the recombinant nucleic acid, and/or a host cell transformed with the vector. In certain embodiments, the vector is an expression vector. Host cells comprising such expression vectors are useful in methods of the invention for producing the mutant or improved polymerase by culturing the host cells under conditions suitable for expression of the recombinant nucleic acid. The polymerases of the invention may be contained in reaction mixtures and/or kits. The embodiments of the recombinant nucleic acids, host cells, vectors, expression vectors, reaction mixtures and kits are as described above and herein.

In yet another aspect, a method for conducting polynucleotide extension is provided. The method generally includes contacting a DNA polymerase having increased 3'-mismatch discrimination as described herein with a primer, a polynucleotide template, and nucleoside triphosphates under conditions suitable for extension of the primer, thereby producing an extended primer. The polynucleotide template can be, for example, an RNA or DNA template. The nucleoside triphosphates can include unconventional nucleotides such as, e.g., ribonucleotides and/or labeled nucleotides. Further, the primer and/or template can include one or more nucleotide analogs. In some variations, the polynucleotide extension method is a method for polynucleotide amplification that includes contacting the mutant or improved DNA polymerase with a primer pair, the polynucleotide template, and the nucleoside triphosphates under conditions suitable for amplification of the polynucleotide. The polynucleotide extension reaction can be, e.g., PCR, isothermal extension, or sequencing (e.g., 454 sequencing reaction).

The present invention also provides a kit useful in such a polynucleotide extension method. Generally, the kit includes at least one container providing a mutant or improved DNA polymerase as described herein. In certain embodiments, the kit further includes one or more additional containers providing one or more additional reagents. For example, in specific variations, the one or more additional containers provide nucleoside triphosphates; a buffer suitable for polynucleotide extension; and/or a primer hybridizable, under polynucleotide extension conditions, to a predetermined polynucleotide template.

Further provided are reaction mixtures comprising the polymerases of the invention. The reactions mixtures can also contain a template nucleic acid (DNA and/or RNA), one or more primer or probe polynucleotides, nucleoside triphosphates (including, e.g., deoxyribonucleotides, ribonucleotides, labeled nucleotides, unconventional nucleotides), buffers, salts, labels (e.g., fluorophores).

Further embodiments of the invention are described herein.

DEFINITIONS

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., *Biochemistry*, 5$^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem*. 65:83-100 and Ibba et al. (2002) "Genetic code: introducing pyrrolysine," *Curr Biol*. 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101(24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al. (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25):14310-14315, Bacher et al. (2001) "Selection and Characterization of *Escherichia coli* Variants Capable of Growth on an Otherwise Toxic Tryptophan Analogue," *J. Bacteriol.* 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51):40324-40328, and Budisa et al. (2001) "Proteins with {beta}-(thienopyrrolyl)alanines as alternative chromophores and pharmaceutically active amino acids," *Protein Sci.* 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "aptamer" refers to a single-stranded DNA that recognizes and binds to DNA polymerase, and efficiently inhibits the polymerase activity as described in U.S. Pat. No. 5,693,502, hereby expressly incorporated by reference herein in its entirety.

The term "mutant," in the context of DNA polymerases of the present invention, means a polypeptide, typically recombinant, that comprises one or more amino acid substitutions relative to a corresponding, naturally-occurring or unmodified DNA polymerase.

The term "unmodified form," in the context of a mutant polymerase, is a term used herein for purposes of defining a mutant DNA polymerase of the present invention: the term "unmodified form" refers to a functional DNA polymerase that has the amino acid sequence of the mutant polymerase except at one or more amino acid position(s) specified as characterizing the mutant polymerase. Thus, reference to a mutant DNA polymerase in terms of (a) its unmodified form and (b) one or more specified amino acid substitutions means that, with the exception of the specified amino acid substitution(s), the mutant polymerase otherwise has an amino acid sequence identical to the unmodified form in the specified motif. The "unmodified polymerase" (and therefore also the modified form having increased 3'-mismatch discrimination) may contain additional mutations to provide desired functionality, e.g., improved incorporation of dideoxyribonucleotides, ribonucleotides, ribonucleotide analogs, dye-labeled nucleotides, modulating 5'-nuclease activity, modulating 3'-nuclease (or proofreading) activity, or the like. Accordingly, in carrying out the present invention as described herein, the unmodified form of a DNA polymerase is predetermined. The unmodified form of a DNA polymerase can be, for example, a wild-type and/or a naturally occurring DNA polymerase, or a DNA polymerase that has already been intentionally modified. An unmodified form of the polymerase is preferably a thermostable DNA polymerases, such as DNA polymerases from various thermophilic bacteria, as well as functional variants thereof having substantial sequence identity to a wild-type or naturally occurring thermostable polymerase. Such variants can include, for example, chimeric DNA polymerases such as, for example, the chimeric DNA polymerases described in U.S. Pat. No. 6,228,628 and U.S. Application Publication No. 2004/0005599, which are incorporated by reference herein in their entirety. In certain embodiments, the unmodified form of a polymerase has reverse transcriptase (RT) activity.

The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species Sps17, *Thermus* species Z05, *Thermus caldophilus, Bacillus caldotenax, Thermotoga neopolitana*, and *Thermosipho africanus*.

The term "thermoactive" refers to an enzyme that maintains catalytic properties at temperatures commonly used for reverse transcription or anneal/extension steps in RT-PCR and/or PCR reactions (i.e., 45-80° C.). Thermostable enzymes are those which are not irreversibly inactivated or denatured when subjected to elevated temperatures necessary for nucleic acid denaturation. Thermoactive enzymes may or may not be thermostable. Thermoactive DNA polymerases can be DNA or RNA dependent from thermophilic species or from mesophilic species including, but not limited to, *Escherichia coli, Moloney murine leukemia viruses*, and *Avian myoblastosis* virus.

As used herein, a "chimeric" protein refers to a protein whose amino acid sequence represents a fusion product of subsequences of the amino acid sequences from at least two distinct proteins. A chimeric protein typically is not produced by direct manipulation of amino acid sequences, but, rather, is expressed from a "chimeric" gene that encodes the chimeric amino acid sequence. In certain embodiments, for example, an unmodified form of a mutant DNA polymerase of the present invention is a chimeric protein that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

In the context of DNA polymerases, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase refers to equivalent positions, based on alignment, in other DNA polymerases and structural homologues and families. In some embodiments of the present invention, "correspondence" of amino acid positions are determined with respect to a region of the polymerase comprising one or more motifs of SEQ ID NO:1, 2, 3, 4, 5, 6, 7, 36, 37, 38, 39, 40, or 41. When a polymerase polypeptide sequence differs from SEQ ID NOS:1, 2, 3, 4, 5, 6, 7, 36, 37, 38, 39, 40, or 41 (e.g., by changes in amino acids or addition or deletion of amino acids), it may be that a particular mutation associated with improved activity as discussed herein will not be in the same position number as it is in SEQ ID NOS:1, 2, 3, 4, 5, 6, 7, 36, 37, 38, 39, 40, or 41. This is illustrated, for example, in Table 1.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "primer" as used herein refers to a polynucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonuceotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISA assays), biotin, or haptens and proteins for which antisera or monoclonal antibodies are available.

The term "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light emitting moiety (e.g., a fluorescent dye, etc.). In certain embodiments, 5'-nuclease probes include regions of self-complementarity such that the probes are capable of forming hairpin structures under selected conditions. To further illustrate, in some embodiments a 5'-nuclease probe comprises at least two labeling moieties and emits radiation of increased intensity after one of the two labels is cleaved or otherwise separated from the oligonucleotide. In certain embodiments, a 5'-nuclease probe is labeled with two different fluorescent dyes, e.g., a 5' terminus reporter dye and the 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission of the reporter dye is no longer quenched. Exemplary 5'-nuclease probes are also described in, e.g., U.S. Pat. No. 5,210,015, entitled "Homogeneous assay system using the nuclease activity of a nucleic acid polymerase," issued May 11, 1993 to Gelfand et al., U.S. Pat. No. 5,994,056, entitled "Homogeneous methods for nucleic acid amplification and detection," issued Nov. 30, 1999 to Higuchi, and U.S. Pat. No. 6,171,785, entitled "Methods and devices for homogeneous nucleic acid amplification and detector," issued Jan. 9, 2001 to Higuchi, which are each incorporated by reference herein. In other embodiments, a 5' nuclease probe may be labeled with two or more different reporter dyes and a 3' terminus quencher dye or moiety.

The term "FRET" or "fluorescent resonance energy transfer" or "Foerster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.).

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-$PO_4$ analogs of ribonucleotides (see, e.g., U.S. Application Publication Nos. 2005/0037991 and 2005/0037398, which are both incorporated by reference). Other unconventional nucleotides include phosphorothioate dNTPs ([[α]-S]dNTPs), 5'-[α]-borano-dNTPs, [α]-methyl-phosphonate dNTPs, and ribonucleoside triphosphates (rNTPs). Unconventional bases may be labeled with radioactive isotopes such as $^{32}P$, $^{33}P$, or $^{35}S$; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare UK Limited (Amersham Place, Little Chalfont, Buckinghamshire, England).

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

The term "mismatch discrimination" refers to the ability of a biocatalyst (e.g., an enzyme, such as a polymerase, ligase, or the like) to distinguish a fully complementary sequence from a mismatch-containing sequence when extending a nucleic acid (e.g., a primer or other oligonucleotide) in a template-dependent manner by attaching (e.g., covalently) one or more nucleotides to the nucleic acid. The term "3'-mismatch discrimination" refers to the ability of a biocatalyst to distinguish a fully complementary sequence from a mismatch-containing (nearly complementary) sequence where the nucleic acid to be extended (e.g., a primer or other oligonucleotide) has a mismatch at the nucleic acid's 3' terminus compared to the template to which the nucleic acid hybridizes. In some embodiments, the nucleic acid to be extended comprises a mismatch at the 3' end relative to the fully complementary sequence. In some embodiments, the nucleic acid to be extended comprises a mismatch at the penultimate (N−1) 3' position and/or at the N−2 position relative to the fully complementary sequence.

The term "Cp value" or "crossing point" value refers to a value that allows quantification of input target nucleic acids. The Cp value can be determined according to the second-derivative maximum method (Van Luu-The, et al., "Improved real-time RT-PCR method for high-throughput measurements using second derivative calculation and double correction," BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region (Van Luu-The, et al., BioTechniques, Vol. 38, No. 2, February 2005, pp. 287-293). These computations are easily carried out by any person skilled in the art.

The term "PCR efficiency" refers to an indication of cycle to cycle amplification efficiency for the perfectly matched primer template. PCR efficiency is calculated for each condition using the equation: % PCR efficiency=$(10^{(-slope)}-1) \times 100$, wherein the slope was calculated by linear regression with the log copy number plotted on the y-axis and Cp plotted on the x-axis.

The term "multiplex" refers to amplification with more than one set of primers, or the amplification of more that one polymorphism site in a single reaction.

BRIEF DESCRIPTION OF THE DRAWINGS

FIG. 1 depicts an amino acid sequence alignment of a region from the polymerase domain of exemplary DNA polymerases from various species of bacteria: *Thermus* species Z05 (Z05) (SEQ ID NO:12), *Thermus aquaticus* (Taq) (SEQ ID NO:13), *Thermus filiformus* (Tfi) (SEQ ID NO:14), *Thermus flavus* (Tfl) (SEQ ID NO:15), *Thermus* species Sps17 (Sps17) (SEQ ID NO:16), *Thermus thermophilus* (Tth) (SEQ ID NO:17), *Thermus caldophilus* (Tca) (SEQ ID NO:18), *Thermotoga maritima* (Tma) (SEQ ID NO:19), *Thermotoga neopolitana* (Tne) (SEQ ID NO:20), *Thermosipho africanus* (Taf) (SEQ ID NO:21), *Deinococcus radiodurans* (Dra) (SEQ ID NO:23), *Bacillus stearothermophilus* (Bst) (SEQ ID NO:24), and *Bacillus caldotenax* (Bca) (SEQ ID NO:25). In addition, the polypeptide regions shown comprise the amino acid motif G-Y-V-$X_1$-T-L-$X_2$-$X_3$-R-$X_4$-$X_5$-$X_6$-$X_7$-P (SEQ ID NO:26), the variable positions of which are further defined herein. This motif is highlighted in bold type for each polymerase sequence. Amino acid positions amenable to mutation in accordance with the present invention are indicated with an asterisk (*).

FIG. 2 provides sequence identities among the following DNA Polymerase I enzymes: *Thermus* sp. Z05 DNA polymerase (Z05); *Thermus aquaticus* DNA polymerase (Taq); *Thermus filiformis* DNA polymerase (Tfi); *Thermus flavus* DNA polymerase (Tfl); *Thermus* sp. Sps17 DNA polymerase (Sps17); *Thermus thermophilus* DNA polymerase (Tth); *Thermus caldophilus* DNA polymerase (Tca); *Deinococcus radiodurans* DNA polymerase (Dra); *Thermotoga maritima* DNA polymerase (Tma); *Thermotoga neopolitana* DNA polymerase (Tne); *Thermosipho africanus* DNA polymerase (Taf); *Bacillus stearothermophilus* DNA polymerase (Bst); and *Bacillus caldotenax* DNA polymerase (Bca). (A) sequence identities over the entire polymerase I enzyme (corresponding to amino acids 1-834 of Z05); and (B) sequence identities over the polymerase sub domain corresponding to amino acids 420-834 of Z05.

DETAILED DESCRIPTION

The present invention provides improved DNA polymerases in which one or more amino acids in the polymerase domain have been identified as improving one or more polymerase activity or characteristics. The DNA polymerases of the invention are active enzymes having increased 3'-mismatch discrimination activity (i.e., the inventive polymerases described herein are less likely to extend primers that are mismatched to template at or near the 3' end of the primer) relative to the unmodified form of the polymerase otherwise identical except for the amino acid difference noted herein. The DNA polymerases are useful in a variety of applications involving polynucleotide extension or amplification of polynucleotide templates, including, for example, applications in recombinant DNA studies and medical diagnosis of disease.

Polymerases of the Invention

In some embodiments, the DNA polymerases of the invention can be characterized by having the following motif:

Gly-Tyr-Val-$X_1$-Thr-Leu-$X_2$-$X_3$-Arg-$X_4$-$X_5$-$X_6$-$X_7$-Pro (also referred to herein in the one-letter code as G-Y-V-$X_1$-T-L-$X_2$-$X_3$-R-$X_4$-$X_5$-$X_6$-$X_7$-P); wherein $X_1$ is Glu (E), Arg (R) or Thr (T);
$X_2$ is Phe (F), Tyr (Y) or Leu (L);
$X_3$ is Gly (G) or His (H);
$X_4$ is Arg (R) or Lys (K);
$X_5$ is any amino acid other than Arg (R);
$X_6$ is Tyr (Y) or Asp (D); and
$X_7$ is Val (V), Ile (I) or Leu (L) (SEQ ID NO:8).

In some embodiments, $X_5$ is selected from G, A, L, M, W, P, S, T, F, Y, C, N, Q, D, E, K, V, I or H (SEQ ID NO:42).

In some embodiments, DNA polymerases of the invention can be characterized by having the following motif (corresponding to Thermus and Thermotoga):

Gly-Tyr-Val-$X_1$-Thr-Leu-Phe-Gly-Arg-$X_4$-$X_5$-$X_6$-$X_7$-Pro (also referred to herein in the one-letter code as G-Y-V-$X_1$-T-L-F-G-R-$X_4$-$X_5$-$X_6$-$X_7$-P); wherein $X_1$ is Glu (E) or Arg (R);
$X_4$ is Arg (R) or Lys (K);
$X_5$ is any amino acid other than Arg (R);
$X_6$ is Tyr (Y) or Asp (D); and
$X_7$ is Val (V) or Ile (I) (SEQ ID NO:9).

In some embodiments, DNA polymerases of the invention can be characterized by having the following motif:

Gly-Tyr-Val-Glu-Thr-Leu-Phe-Gly-Arg-Arg-$X_a$-Tyr-Val-Pro (also referred to herein in the one-letter code as G-Y-V-E-T-L-F-G-R-R-$X_a$-Y-V-P); wherein $X_5$ is any amino acid other than Arg (R) (SEQ ID NO:10).

In some embodiments, DNA polymerases of the invention can be characterized by having the following motif:

Gly-Tyr-Val-Glu-Thr-Leu-Phe-Gly-Arg-Arg-$X_5$-Tyr-Val-Pro (also referred to herein in the one-letter code as G-Y-V-E-T-L-F-G-R-R-$X_{a5}$-Y-V-P); wherein $X_5$ is Ala (A), Cys (C), Asp (D), Gly (G), or Asn (N) (SEQ ID NO:11).

This motif is present within the "fingers" domain of many Family A type DNA-dependent DNA polymerases, particularly thermostable DNA polymerases from thermophilic bacteria (Li et al., EMBO J. 17:7514-7525, 1998). For example, FIG. 1 shows an amino acid sequence alignment comprising the native sequence corresponding to the motif above in DNA polymerases from several species of bacteria: Escherichia coli, Bacillus caldotenax, Bacillus stearothermophilus, Deinococcus radiodurans, Thermosipho africanus, Thermotoga maritima, Thermotoga neopolitana, Thermus aquaticus, Thermus caldophilus, Thermus filiformis, Thermus flavus, Thermus sp. Sps17, Thermus sp. Z05, and Thermus thermophilus. As shown, the motif of SEQ ID NO:8 (except where $X_5$ is R) is present in each of these polymerases, indicating a conserved function for this region of the polymerase. FIG. 2 provides sequence identities among these DNA polymerases.

Accordingly, in some embodiments, the invention provides for a polymerase comprising SEQ ID NO:8, 9, 10, or 11 (e.g., where $X_5$ is selected, as appropriate based on the consensus sequence, from G, A, L, M, W, P, S, T, F, Y, C, N, Q, D, E, K, V, I or H), having the improved activity and/or characteristics described herein, and wherein the DNA polymerase is otherwise a wild-type or a naturally occurring DNA polymerase, such as, for example, a polymerase from any of the species of thermophilic bacteria listed above, or is substantially identical to such a wild-type or a naturally occurring DNA polymerase. For example, in some embodiments, the polymerase of the invention comprises SEQ ID NO:8, 9, 10, or 11 and is at least 80%, 85%, 90%, or 95% identical to SEQ ID NO:1, 2, 3, 4, 5, 6, 7, 36, 37, 38, 39, 40, or 41. In one variation, the unmodified form of the polymerase is from a species of the genus Thermus. In some embodiments of the invention, the unmodified polymerase is from a thermophilic species other than Thermus, e.g., Thermotoga. The full nucleic acid and amino acid sequence for numerous thermostable DNA polymerases are available. The sequences each of Thermus aquaticus (Taq) (SEQ ID NO:2), Thermus thermophilus (Tth) (SEQ ID NO:6), Thermus species Z05 (SEQ ID NO:1), Thermus species Sps17 (SEQ ID NO:5), Thermotoga maritima (Tma) (SEQ ID NO:38), and Thermosipho africanus (Taf) (SEQ ID NO:37) polymerase have been published in PCT International Patent Publication No. WO 92/06200, which is incorporated herein by reference. The sequence for the DNA polymerase from Thermus flavus (SEQ ID NO:4) has been published in Akhmetzjanov and Vakhitov (Nucleic Acids Research 20:5839, 1992), which is incorporated herein by reference. The sequence of the thermostable DNA polymerase from Thermus caldophilus (SEQ ID NO:7) is found in EMBL/GenBank Accession No. U62584. The sequence of the thermostable DNA polymerase from Thermus filiformis can be recovered from ATCC Deposit No. 42380 using, e.g., the methods provided in U.S. Pat. No. 4,889,818, as well as the sequence information provided in Table 1. The sequence of the Thermotoga neapolitana DNA polymerase (SEQ ID NO:39) is from GeneSeq Patent Data Base Accession No. R98144 and PCT WO 97/09451, each incorporated herein by reference. The sequence of the thermostable DNA polymerase from Bacillus caldotenax (SEQ ID NO:41) is described in, e.g., Uemori et al. (J Biochem (Tokyo) 113(3): 401-410, 1993; see also, Swiss-Prot database Accession No. Q04957 and GenBank Accession Nos. D12982 and BAA02361), which are each incorporated by reference. Examples of unmodified forms of DNA polymerases that can be modified as described herein are also described in, e.g., U.S. Pat. No. 6,228,628, entitled "Mutant chimeric DNA polymerase" issued May 8, 2001 to Gelfand et al.; U.S. Pat. No. 6,346,379, entitled "Thermostable DNA polymerases incorporating nucleoside triphosphates labeled with fluorescein family dyes" issued Feb. 12, 2002 to Gelfand et al.; U.S. Pat. No. 7,030,220, entitled "Thermostable enzyme promoting the fidelity of thermostable DNA polymerases-for improvement of nucleic acid synthesis and amplification in vitro" issued Apr. 18, 2006 to Ankenbauer et al.; U.S. Pat. No. 6,881,559, entitled "Mutant B-type DNA polymerases exhibiting improved performance in PCR" issued Apr. 19, 2005 to Sobek et al.; U.S. Pat. No. 6,794,177, entitled "Modified DNA-polymerase from carboxydothermus hydrogenoformans and its use for coupled reverse transcription and polymerase chain reaction" issued Sep. 21, 2004 to Markau et al.; 6,468,775, entitled "Thermostable DNA polymerase from carboxydothermus hydrogenoformans" issued Oct. 22, 2002 to Ankenbauer et al.; and U.S. Pat. Appl. Nos. 20040005599, entitled "Thermostable or thermoactive DNA polymerase molecules with attenuated 3'-5' exonuclease activity" filed Mar. 26, 2003 by Schoenbrunner et al.; 20020012970, entitled "High temperature reverse transcription using mutant DNA polymerases" filed Mar. 30, 2001 by Smith et al.; 20060078928, entitled "Thermostable enzyme promoting the fidelity of thermostable DNA polymerases-for improvement of nucleic acid synthesis and amplification in vitro" filed Sep. 29, 2005 by Ankenbauer et al.; 20040115639, entitled "Reversibly modified thermostable enzymes for DNA synthesis and amplification in vitro" filed Dec. 11, 2002 by Sobek et al., which are each incorporated by reference. Representative full length polymerase sequences are also provided in the sequence listing.

In some embodiments, the polymerase of the invention, as well as having a polymerase domain comprising SEQ ID NOS:8, 9, 10, or 11, also comprises a nuclease domain (e.g., corresponding to positions 1 to 291 of Z05).

In some embodiments, a polymerase of the invention is a chimeric polymerase, i.e., comprising polypeptide regions from two or more enzymes. Examples of such chimeric DNA polymerases are described in, e.g., U.S. Pat. No. 6,228,628, which is incorporated by reference herein in its entirety. Particularly suitable are chimeric CS-family DNA polymerases, which include the CS5 (SEQ ID NO:29) and CS6 (SEQ ID NO:30) polymerases and variants thereof having substantial sequence identity or similarity to SEQ ID NO:29 or SEQ ID NO:30 (typically at least 80% sequence identity and more typically at least 90%, 91%, 92%, 93%, 94%, 95%, 96%, 97%, 98% or 99% sequence identity) and can thus be modified to contain SEQ ID NO:8. The CS5 and CS6 DNA polymerases are chimeric enzymes derived from *Thermus* sp. Z05 and *Thermotoga maritima* (Tma) DNA polymerases. They comprise the N-terminal 5'-nuclease domain of the *Thermus* enzyme and the C-terminal 3'-5' exonuclease and the polymerase domains of the Tma enzyme. These enzymes have efficient reverse transcriptase activity, can extend nucleotide analog-containing primers, and can utilize alpha-phosphorothioate dNTPs, dUTP, dITP, and also fluorescein- and cyanine-dye family labeled dNTPs. The CS5 and CS6 polymerases are also efficient $Mg^{2+}$-activated PCR enzymes. The CS5 and CS6 chimeric polymerases are further described in, e.g., U.S. Pat. Application Publication No. 2004/0005599, which is incorporated by reference herein in its entirety.

In some embodiments, the polymerase of the invention comprises SEQ ID NO:8, 9, 10, or 11 and further comprises one or more additional amino acid changes (e.g., by amino acid substitution, addition, or deletion) compared to a native polymerase. In some embodiments, such polymerases retain the amino acid motif of SEQ ID NO:8 (or a motif of SEQ ID NO:9, 10 or 11), and further comprise the amino acid motif of SEQ ID NO:27 (corresponding to the D580X mutation of Z05 (SEQ ID NO:1)) as follows:

T-G-R-L-SS-$X_7$-$X_8$-P-N-L-Q-N; wherein $X_7$ is Ser (S) or Thr (T); and $X_8$ is any amino acid other than D or E (SEQ ID NO:27)

The mutation characterized by SEQ ID NO:27 is discussed in more detail in, e.g., US Patent Publication No. 2009/0148891. In some embodiments, such functional variant polymerases typically will have substantial sequence identity or similarity to the wild-type or naturally occurring polymerase (e.g., SEQ ID NO: 1, 2, 3, 4, 5, 6, 7, 39, 40, 41, 42, 43, or 44), typically at least 80% sequence identity and more typically at least 90%, 91%, 92%, 93%, 94%, 95%, 96%, 97%, 98% or 99% sequence identity.

In some embodiments, the amino acid at position $X_5$ is substituted with an amino acid as set forth in SEQ ID NO:8, 9, 10 or 11, and the amino acid at position $X_8$ is substituted with an amino acid as set forth in SEQ ID NO:27. Thus, in some embodiments, the amino acid at position $X_5$ is any amino acid other than Arg (R) and the amino acid at position $X_8$ is any amino acid other than Asp (D) or Glu (E). In some embodiments, amino acid substitutions include Leucine (L), Glycine (G), Threonine (T), Glutamine (Q), Alanine (A), Serine (S), Asparagine (N), Arginine (R), and Lysine (K) at position $X_8$ of SEQ ID NO:27. In certain embodiments, amino acid substitutions independently include Alanine (A), Cysteine (C), Aspartic Acid (D), Glycine (G), or Asparagine (N) at position $X_5$, and Glycine (G) at position $X_8$. Other suitable amino acid substitution(s) at one or more of the identified sites can be determined using, e.g., known methods of site-directed mutagenesis and determination of polynucleotide extension performance in assays described further herein or otherwise known to persons of skill in the art.

Because the precise length of DNA polymerases vary, the precise amino acid positions corresponding to each of $X_5$ and $X_8$ can vary depending on the particular polymerase used. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention. The positions corresponding to each of $X_5$ and $X_8$ are shown in Table 1 for representative chimeric thermostable DNA polymerases and thermostable DNA polymerases from exemplary thermophilic species.

TABLE 1

Amino Acid Positions Corresponding to Motif Positions $X_5$ (e.g., of SEQ ID NOS: 8, 9, 10, and 11) and $X_8$ (of SEQ ID NO: 27) in Exemplary Polymerases.

| Organism or Chimeric Sequence | Amino Acid Position | |
|---|---|---|
| Consensus (SEQ ID NO:) | $X_5$ | $X_8$ (of SEQ ID NO: 27) |
| T. thermophilus (6) | 730 | 580 |
| T. caldophilus (7) | 730 | 580 |
| T. sp. Z05 (1) | 730 | 580 |
| T. aquaticus (2) | 728 | 578 |
| T. flavus (4) | 727 | 577 |
| T. filiformis (3) | 726 | 576 |
| T. sp. Sps17 (5) | 726 | 576 |
| T. maritima (38) | 791 | 640 |
| T. neapolitana (39) | 791 | 640 |
| T. africanus (37) | 790 | 639 |
| B. caldotenax (41) | 772 | 621 |
| B. stearothermophilus (40) | 771 | 620 |
| CS5 (29) | 791 | 640 |
| CS6 (30) | 791 | 640 |

In some embodiments, the DNA polymerase of the present invention is derived from *Thermus* sp. Z05 DNA polymerase (SEQ ID NO:1) or a variant thereof (e.g., carrying the D580G mutation or the like). As referred to above, in *Thermus* sp. Z05 DNA polymerase, position $X_5$ corresponds to Arginine (R) at position 730; position $X_8$ corresponds to Aspartate (D) at position 580. Thus, in certain variations of the invention, the mutant polymerase comprises at least one amino acid substitution, relative to a *Thermus* sp. Z05 DNA polymerase, at R730 and D580. Thus, typically, the amino acid at position 730 is not R. In some embodiments, the amino acid at position 730 is selected from G, A, V, L, I, M, F, W, P, S, T, C, Y, N, Q, D, E, K, or H. In certain embodiments, the amino acid residue at position 730 is A, C, D, G, or N. In certain embodiments, amino acid residues at position D580 can be selected from Leucine (L), Glycine (G), Threonine (T), Glutamine (Q), Alanine (A), Serine (S), Asparagine (N), Arginine (R), and Lysine (K). Exemplary *Thermus* sp. Z05 DNA polymerase mutants include those comprising the amino acid substitution(s) R730A, R730C, R730D, R730G, or R730N and D580G.

In some embodiments, the DNA polymerase of the invention comprises an amino acid at the position corresponding to position 730 of SEQ ID NO:1 that does not have a polar, positively-charged side-chain (e.g., R) at neutral pH (e.g., about pH 7.4). In some embodiments, the DNA polymerase of the invention is derived from a *Thermus* species, and the amino acid at the position corresponding to position 730 of SEQ ID NO:1 is an amino acid having a nonpolar, uncharged side-chain (e.g., G, A, L, M, W, P, F, C, V, or I), an amino acid having a polar, uncharged side-chain (e.g., N, Q, H, S, T, or Y), or an amino acid having a polar, negatively-charged side-chain (e.g., D or E), at neutral pH. In some embodiments, the amino acid at the position corresponding to position 730 of SEQ ID NO:1 having a nonpolar, uncharged side-chain is A, C, or G. In some embodiments, the amino acid at the position corresponding to position 730 of SEQ ID NO:1 having a polar, uncharged side-chain is N. In some embodiments, the amino acid at the position corresponding to position 730 of SEQ ID NO:1 having a polar, negatively-charged side-chain is D.

In some embodiments, the DNA polymerases of the present invention can also include other, non-substitutional modification(s). Such modifications can include, for example, covalent modifications known in the art to confer an additional advantage in applications comprising polynucleotide extension. For example, in certain embodiments, the mutant DNA polymerase further includes a thermally reversible covalent modification. DNA polymerases comprising such thermally reversible modifications are particularly suitable for hot-start applications, such as, e.g., various hot-start PCR techniques. Thermally reversible modifier reagents amenable to use in accordance with the mutant DNA polymerases of the present invention are described in, for example, U.S. Pat. No. 5,773,258 to Birch et al., which is incorporated by reference herein.

For example, particularly suitable polymerases comprising a thermally reversible covalent modification are produced by a reaction, carried out at alkaline pH at a temperature which is less than about 25° C., of a mixture of a thermostable enzyme and a dicarboxylic acid anhydride having a general formula as set forth in the following formula I:

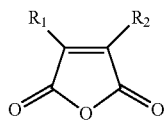

where $R_1$ and $R_2$ are hydrogen or organic radicals, which may be linked; or having the following formula II:

where $R_1$ and $R_2$ are organic radicals, which may linked, and the hydrogens are cis, essentially as described in Birch et al, supra.

The DNA polymerases of the present invention can be constructed by mutating the DNA sequences that encode the corresponding unmodified polymerase (e.g., a wild-type polymerase or a corresponding variant from which the polymerase of the invention is derived), such as by using techniques commonly referred to as site-directed mutagenesis. Nucleic acid molecules encoding the unmodified form of the polymerase can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the polymerase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Mutant DNA polymerases with more than one amino acid substituted can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified polymerase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids encoding any of the DNA polymerases of the present invention (e.g., polymerases comprising any of SEQ ID NOS:8, 9, 10, or 11). Using a nucleic acid of the present invention, encoding a DNA polymerase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant DNA polymerase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the polymerase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant polymerase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a DNA polymerase of the invention is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, viral infection, and the like.

In some embodiments, prokaryotes are used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

In some embodiments, the DNA polymerases of the present invention are produced by culturing a host cell transformed with an expression vector containing a nucleic acid encoding the DNA polymerase, under the appropriate conditions to induce or cause expression of the DNA polymerase. Methods of culturing transformed host cells under conditions suitable for protein expression are well-known in the art (see, e.g., Sambrook et al., supra). Suitable host cells for production of the polymerases from lambda pL promotor-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the polymerase can be harvested and isolated. Methods for purifying the thermostable DNA polymerase are described in, for example, Lawyer et al., supra.

Once purified, a DNA polymerase's 3' mismatch discrimination can be assayed. For example, in some embodiments, 3' mismatch discrimination activity is determined by comparing the amplification of a target sequence perfectly matched to the primer to amplification of a target that has a single base mismatch at the 3' end of the primer. Amplification can be detected, for example, in real time by use of TaqMan™ probes. Ability of a polymerase to distinguish between the two target sequences can be estimated by comparing the Cps of the two reactions. Optionally, simultaneous amplification of a second target gene in each well can be performed and detected in a second optical channel as a control. "Delta Cp values" refer to the difference in value between the Cp associated with the mismatched template minus the Cp of the matched target (see, e.g., the Examples). In some embodiments, the improved polymerases of the invention have a delta Cp value of at least 1, 2, 3, 4, 5, or more compared to an otherwise identical control polymerase having a native amino acid (e.g., R) at position X5 of SEQ ID NO:8. In some embodiments, this determination is made with the precise materials and conditions set forth in the Examples.

Methods of the Invention

The improved DNA polymerases of the present invention may be used for any purpose in which such enzyme activity is necessary or desired. The improved DNA polymerase can be a thermoactive or thermostable DNA polymerase, as described herein. Accordingly, in one aspect of the invention, methods of polynucleotide extension, including PCR, using the polymerases of the invention are provided. In some embodiments, the invention provides a thermoactive DNA polymerase that is useful to extend an RNA or DNA template when amplification of the template nucleic acid is not required, for example, when it is desired to immediately detect the presence of a target nucleic acid. In some embodiments, the invention provides a thermostable DNA polymerase that is useful when it is desired to extend and/or amplify a target nucleic acid. Conditions suitable for polynucleotide extension are known in the art. (See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the mutant DNA polymerase and nucleoside triphosphates in a suitable environment to permit the addition of one or more nucleotides to the 3' end of the primer, thereby producing an extended primer complementary to the target nucleic acid. The primer can include, e.g., one or more nucleotide analog(s). In addition, the nucleoside triphosphates can be conventional nucleotides, unconventional nucleotides (e.g., ribonucleotides or labeled nucleotides), or a mixture thereof. In some variations, the polynucleotide extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; *PCR Applications: Protocols for Functional Genomics* (Innis et al. eds., Academic Press 1999).

In some embodiments, use of the present polymerases, which provide increased 3' mismatch discrimination, allow for, e.g., rare allele detection. For example, the fidelity of 3' mismatch discrimination of a particular polymerase sets its sensitivity (ability to accurately detect small quantities of a target sequence in the presence of larger quantities of a different but related non-target sequence). Thus, increased 3'-mismatch discrimination results in greater sensitivity for detection of rare alleles. Rare allele detection is useful, for example, when screening biopsies or other samples for rare genetic changes, e.g., a cell carrying a cancer allele in a mass of normal cells.

In some embodiments, the improved polymerases are used for polynucleotide extension in the context of allele specific PCR or single nucleotide polymorphism (SNP) detection. Exemplary SNP detection methods are described in Chen et al., "Single nucleotide polymorphism genotyping: biochemistry, protocol, cost and throughput" Pharmacogenomics J. 3(2):77-96 (2003); Kwok et al., "Detection of single nucleotide polymorphisms" Curr. Issues Mol. Biol. 5(2):43-60 (April 2003); Shi, "Technologies for individual genotyping: detection of genetic polymorphisms in drug targets and disease genes" Am. J. Pharmacogenomics 2(3): 197-205 (2002); and Kwok, "Methods for genotyping single nucleotide polymorphisms" Annu. Rev. Genomics Hum. Genet. 2:235-58 (2001). Exemplary techniques for high-throughput SNP detection are described in Marnellos, "High-throughput SNP analysis for genetic association studies" Curr. Opin. Drug Discov. Devel. 6(3):317-21 (May 2003). Common SNP detection methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Detection of multiple different alleles can also be accomplished using multiplex reactions, which allow the detection of multiple different alleles in a single reaction. In multiplex reactions, two or more allele-specific primers are used to extend and amplify SNPs or multiple nucleotide polymorphisms or alleles. Exemplary methods for multiplex detection of single and multiple nucleotide polymorphisms are described in U.S. Patent Publication No. 2006/0172324, the contents of which are expressly incorporated by reference herein in its entirety.

Other methods for detecting extension products or amplification products using the improved polymerases described herein include the use of fluorescent double-stranded nucleotide binding dyes or fluorescent double-stranded nucleotide intercalating dyes. Examples of fluorescent double-stranded DNA binding dyes include SYBR-green (Molecular Probes). Examples of fluorescent double-stranded intercalating dyes include ethidium bromide. The double stranded DNA binding dyes can be used in conjunction with melting curve analysis to measure primer extension products and/or amplification products. The melting curve analysis can be performed on a real-time PCR instrument, such as the ABI 5700/7000 (96 well format) or ABI 7900 (384 well format) instrument with onboard software (SDS 2.1). Alternatively, the melting curve analysis can be performed as an end point analysis. Exemplary methods of melting point analysis are described in U.S. Patent Publication No. 2006/0172324, the contents of which are expressly incorporated by reference herein in its entirety.

In yet other embodiments, the polymerases of the invention are used for primer extension in the context of DNA sequencing, DNA labeling, or labeling of primer extension products. For example, DNA sequencing by the Sanger dideoxynucleotide method (Sanger et al., *Proc. Natl. Acad. Sci. USA* 74: 5463, 1977) is improved by the present invention for polymerases capable of incorporating unconventional, chain-terminating nucleotides. Advances in the basic Sanger et al. method have provided novel vectors (Yanisch-Perron et al., Gene 33:103-119, 1985) and base analogues (Mills et al., *Proc. Natl. Acad. Sci. USA* 76:2232-2235, 1979; and Barr et al., *Biotechniques* 4:428-432, 1986). In general, DNA sequencing requires template-dependent primer extension in the presence of chain-terminating base analogs, resulting in a distribution of partial fragments that are subsequently separated by size. The basic dideoxy sequencing procedure involves (i) annealing an oligonucleotide primer, optionally labeled, to a template; (ii) extending the primer with DNA polymerase in four separate reactions, each containing a mixture of unlabeled dNTPs and a limiting amount of one chain terminating agent such as a ddNTP, optionally labeled; and (iii) resolving the four sets of reaction products on a high-resolution denaturing polyacrylamide/urea gel. The reaction products can be detected in the gel by autoradiography or by fluorescence detection, depending on the label used, and the image can be examined to infer the nucleotide sequence. These methods utilize DNA polymerase such as the Klenow fragment of *E. coli* Pol I or a modified T7 DNA polymerase.

The availability of thermostable polymerases, such as Taq DNA polymerase, resulted in improved methods for sequencing with thermostable DNA polymerase (see Innis et al., *Proc. Natl. Acad. Sci. USA* 85:9436, 1988) and modifications thereof referred to as "cycle sequencing" (Murray, *Nuc Acids Res.* 17:8889, 1989). Accordingly, thermostable polymerases of the present invention can be used in conjunction with such methods. As an alternative to basic dideoxy sequencing, cycle sequencing is a linear, asymmetric amplification of target sequences complementary to the template sequence in the presence of chain terminators. A single cycle produces a family of extension products of all possible lengths. Following denaturation of the extension reaction product from the DNA template, multiple cycles of primer annealing and primer extension occur in the presence of terminators such as ddNTPs. Cycle sequencing requires less template DNA than conventional chain-termination sequencing. Thermostable DNA polymerases have several advantages in cycle sequencing; they tolerate the stringent annealing temperatures which are required for specific hybridization of primer to nucleic acid targets as well as tolerating the multiple cycles of high temperature denaturation which occur in each cycle, e.g., 90-95° C. For this reason, AMPLITAQ® DNA Polymerase and its derivatives and descendants, e.g., AmpliTaq CS DNA Polymerase and AmpliTaq FS DNA Polymerase have been included in Taq cycle sequencing kits commercialized by companies such as Perkin-Elmer (Norwalk, Conn.) and Applied Biosystems (Foster City, Calif.).

The improved polymerases find use in 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Variations of chain termination sequencing methods include dye-primer sequencing and dye-terminator sequencing. In dye-primer sequencing, the ddNTP terminators are unlabeled, and a labeled primer is utilized to detect extension products (Smith et al., *Nature* 32:674-679, 1986). In dye-terminator DNA sequencing, a DNA polymerase is used to incorporate dNTPs and fluorescently labeled ddNTPs onto the end of a DNA primer (Lee et al., *Nuc. Acids. Res.* 20:2471, 1992). This process offers the advantage of not having to synthesize dye labeled primers. Furthermore, dye-terminator reactions are more convenient in that all four reactions can be performed in the same tube.

Both dye-primer and dye-terminator methods may be automated using an automated sequencing instrument produced by Applied Biosystems (Foster City, Calif.) (U.S. Pat. No. 5,171,534, which is herein incorporated by reference). When using the instrument, the completed sequencing reaction mixture is fractionated on a denaturing polyacrylamide gel or capillaries mounted in the instrument. A laser at the bottom of the instrument detects the fluorescent products as they are electrophoretically separated according to size through the gel.

Two types of fluorescent dyes are commonly used to label the terminators used for dye-terminator sequencing-negatively charged and zwitterionic fluorescent dyes. Negatively charged fluorescent dyes include those of the fluorescein and BODIPY families. BODIPY dyes (4,4-difluoro-4-bora-3a,4a-diaza-s-indacene) are described in International Patent Publication WO 97/00967, which is incorporated herein by reference. Zwitterionic fluorescent dyes include those of the rhodamine family. Commercially available cycle sequencing kits use terminators labeled with rhodamine derivatives. However, the rhodamine-labeled terminators are rather costly and the product must be separated from unincorporated dye-ddNTPs before loading on the gel since they co-migrate with the sequencing products. Rhodamine dye family terminators seem to stabilize hairpin structures in GC-rich regions, which causes the products to migrate anomalously. This can involve the use of dITP, which relaxes the secondary structure but also affects the efficiency of incorporation of terminator.

In contrast, fluorescein-labeled terminators eliminate the separation step prior to gel loading since they have a greater net negative charge and migrate faster than the sequencing products. In addition, fluorescein-labeled sequencing products have better electrophoretic migration than sequencing products labeled with rhodamine. Although wild-type Taq DNA polymerase does not efficiently incorporate terminators labeled with fluorescein family dyes, this can now be accomplished efficiently by use of the modified enzymes as described in U.S. Patent Application Publication No. 2002/0142333, which is incorporated by reference herein in its entirety. Accordingly, modifications as described in US 2002/0142333 can be used in the context of the present invention to produce fluorescein-family-dye-incorporating thermostable polymerases having improved primer extension rates. For example, in certain embodiments, the unmodified DNA polymerase in accordance with the present invention is a modified thermostable polymerase as described in US 2002/0142333 and having the motif set forth in SEQ ID NO:8 (or a motif of SEQ ID NO:9, 10 or 11), and optionally the motif of SEQ ID NO:27.

Other exemplary nucleic acid sequencing formats in which the mutant DNA polymerases of the invention can be used include those involving terminator compounds that include 2'-PO$_4$ analogs of ribonucleotides (see, e.g., U.S. Application Publication Nos. 2005/0037991 and 2005/0037398, and U.S. patent application Ser. No. 12/174,488, which are each incorporated by reference).

Kits

In another aspect of the present invention, kits are provided for use in primer extension methods described herein. In some embodiments, the kit is compartmentalized for ease of use and contains at least one container providing a DNA polymerase of the invention having increased 3' mismatch discrimination in accordance with the present invention. One or more additional containers providing additional reagent(s) can also be included. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. For example, in certain embodiments, the kit further includes a container providing a 5' sense primer hybridizable, under primer extension conditions, to a predetermined polynucleotide template, or a primer pair comprising the 5' sense primer and a corresponding 3' antisense primer. In some embodiments, the kit includes one or more containers containing one or more primers that are fully complementary to single nucleotide polymorphisms or multiple nucleotide polymorphisms, wherein the primers are useful for multiplex reactions, as described above. In other, non-mutually exclusive variations, the kit includes one or more containers providing nucleoside triphosphates (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction. In some embodiments, the kit includes one or more labeled or unlabeled probes. Examples of probes include dual-labeled FRET (fluorescence resonance energy transfer) probes and molecular beacon probes. In another embodiment, the kit contains an aptamer, e.g., for hot start PCR assays.

Reaction Mixtures

In another aspect of the present invention, reaction mixtures are provided comprising the polymerases with increased 3'-mismatch discrimination activity, as described herein. The reaction mixtures can further comprise reagents for use in, e.g., nucleic acid amplification procedures (e.g., PCR, RT-PCR), DNA sequencing procedures, or DNA labeling procedures. For example, in certain embodiments, the reaction mixtures comprise a buffer suitable for a primer extension reaction. The reaction mixtures can also contain a template nucleic acid (DNA and/or RNA), one or more primer or probe polynucleotides, nucleoside triphosphates (including, e.g., deoxyribonucleotides, ribonucleotides, labeled nucleotides, unconventional nucleotides), salts (e.g., $Mn^{2+}$, $Mg^{2+}$), and labels (e.g., fluorophores). In some embodiments, the reaction mixture further comprises double stranded DNA binding dyes, such as SYBR green, or double stranded DNA intercalating dyes, such as ethidium bromide. In some embodiments, the reaction mixtures contain a 5'-sense primer hybridizable, under primer extension conditions, to a predetermined polynucleotide template, or a primer pair comprising the 5'-sense primer and a corresponding 3' antisense primer. In certain embodiments, the reaction mixture further comprises a fluorogenic FRET hydrolysis probe for detection of amplified template nucleic acids, for example a Taqman® probe. In some embodiments, the reaction mixture contains two or more primers that are fully complementary to single nucleotide polymorphisms or multiple nucleotide polymorphisms. In some embodiments, the reaction mixtures contain alpha-phosphorothioate dNTPs, dUTP, dITP, and/or labeled dNTPs such as, e.g., fluorescein- or cyanin-dye family dNTPs.

EXAMPLES

The following examples are offered to illustrate, but not to limit the claimed invention.

Example 1: Identification of Mutant DNA Polymerases with Increased 3'-Mismatch Discrimination This example illustrates that various amino acid substitutions at the R730 position of Z05 DNA polymerase result in increased 3'-mismatch discrimination.

The control DNA polymerase of this example is a *Thermus* sp. Z05 DNA polymerase of SEQ ID NO:1 except that the amino acid at position 580 is glycine (e.g., a D580G substitution) (hereinafter Z05 D580G polymerase).

Mutations in Z05 D580G polymerase were identified that provide a reduced ability to extend an oligonucleotide primer with a 3'-mismatch to a template. In brief, the steps in this screening process included library generation, expression and partial purification of the mutant enzymes, screening of the enzymes for the desired property, DNA sequencing, clonal purification, and further characterization of selected candidate mutants. Each of these steps is described further below.

Clonal Library Generation:

A nucleic acid encoding the polymerase domain of Z05 D580G DNA polymerase was subjected to error-prone (mutagenic) PCR between Blp I and Bgl II restriction sites of a plasmid including this nucleic acid sequence. The amplified sequence is provided as SEQ ID NO:33. The primers used for this are given below:

```
Forward Primer:
                             (SEQ ID NO: 31)
5'-CTACCTCCTGGACCCCTCCAA-3';
and, Reverse Primer:
                             (SEQ ID NO: 32)
5'-ATAACCAACTGGTAGTGGCGTGTAA-3'.
```

PCR was performed using a range of $Mg^{2+}$ concentrations from 1.8-3.6 mM, in order to generate libraries with a range of mutation rates. Buffer conditions were 50 mM Bicine pH 8.2, 115 mM KOAc, 8% w/v glycerol, and 0.2 mM each dNTPs. A GeneAmp® AccuRT Hot Start PCR enzyme was used at 0.15 U/μL. Starting with $5 \times 10^5$ copies of linearized Z05 D580G plasmid DNA per reaction volume of 50 reactions were denatured using a temperature of 94° C. for 60 seconds, then 30 cycles of amplification were performed, using a denaturation temperature of 94° C. for 15 seconds, an annealing temperature of 60° C. for 15 seconds, an extension temperature of 72° C. for 120 seconds, and followed by a final extension at a temperature of 72° C. for 5 minutes.

The resulting amplicon was purified with a QIAquick PCR Purification Kit (Qiagen, Inc., Valencia, Calif., USA) and cut with Blp I and Bgl II, and then re-purified with a QIAquick PCR Purification Kit. A Z05 D580G vector plasmid was prepared by cutting with the same two restriction enzymes and treating with alkaline phosphatase, recombinant (RAS, cat#03359123001) and purified with a QIAquick PCR Purification Kit. The cut vector and the mutated insert were mixed at a 1:3 ratio and treated with T4 DNA ligase for 5 minutes at room temperature (NEB Quick Ligation™ Kit). The ligations were purified with a QIAquick PCR Purification Kit and transformed into an *E. coli* host strain by electroporation.

Aliquots of the expressed cultures were plated on ampicillin-selective medium in order to determine the number of unique transformants in each transformation. Transformations were stored at −70° C. to −80° C. in the presence of glycerol as a cryo-protectant.

Each library was then spread on large format ampicillin-selective agar plates. Individual colonies were transferred to 384-well plates containing 2× Luria broth with ampicillin and 10% w/v glycerol using an automated colony picker (QPix2, Genetix Ltd). These plates were incubated overnight at 30° C. to allow the cultures to grow and then stored at −70° C. to −80° C. The glycerol added to the 2× Luria broth was low enough to permit culture growth and yet high enough to provide cryo-protection. Several thousand colonies at several mutagenesis ($Mg^{2+}$) levels were prepared in this way for later use.

Extract Library Preparation Part 1—Fermentation:

From the clonal libraries described above, a corresponding library of partially purified extracts suitable for screening purposes was prepared. The first step of this process was to make small-scale expression cultures of each clone. These cultures were grown in 96-well format; therefore there were 4 expression culture plates for each 384-well library plate. 0.5 μL was transferred from each well of the clonal library plate to a well of a 96 well seed plate, containing 150 μL of Medium A (see Table 3 below). This seed plate was shaken overnight at 1150 rpm at 30° C., in an iEMS plate incubator/shaker (ThermoElectron). These seed cultures were then used to inoculate the same medium, this time inoculating 20 μL into 250 μL Medium A in large format 96 well plates (Nunc #267334). These plates were incubated overnight at 37° C. with shaking. The expression plasmid contained transcriptional control elements, which allow for expression at 37° C. but not at 30° C. After overnight incubation, the cultures expressed the clone protein at typically 1-10% of total cell protein. The cells from these cultures were harvested by centrifugation. These cells were either frozen (−20° C.) or processed immediately, as described below.

TABLE 2

| Medium A (Filter-sterilized prior to use) | |
|---|---|
| Component | Concentration |
| $MgSO_4 \cdot 7H_2O$ | 0.2 g/L |
| Citric acid·$H_2O$ | 2 g/L |
| $K_2HPO_4$ | 10 g/L |
| $NaNH_4PO_4 \cdot 4H_2O$ | 3.5 g/L |
| $MgSO_4$ | 2 mM |
| Casamino acids | 2.5 g/L |
| Glucose | 2 g/L |
| Thiamine·HCl | 10 mg/L |
| Ampicillin | 100 mg/L |

Extract Library Preparation Part 2—Extraction:

Cell pellets from the fermentation step were resuspended in 25 μL Lysis buffer (Table 3 below) and transferred to 384-well thermocycler plates and sealed. Note that the buffer contained lysozyme to assist in cell lysis, and DNase to remove DNA from the extract. To lyse the cells the plates were incubated at 37° C. for 15 minutes, frozen overnight at −20° C., and incubated again at 37° C. for 15 minutes. Ammonium sulfate was added (1.5 μL of a 2 M solution) and the plates incubated at 75° C. for 15 minutes in order to precipitate and inactivate contaminating proteins, including the exogenously added nucleases. The plates were centrifuged at 3000×g for 15 minutes at 4° C. and the supernatants transferred to a fresh 384-well thermocycler plate. These extract plates were frozen at −20° C. for later use in screens. Each well contained about 0.5-3 µM of the mutant library polymerase enzyme.

TABLE 3

Lysis Buffer

| Component | Concentration or Percentage |
|---|---|
| Tris pH 7.5 | 50 mM |
| EDTA | 1 mM |
| MgCl$_2$ | 6 mM |
| Tween 20 | 0.5% v/v |
| Lysozyme (from powder) | 1 mg/mL |
| DNase I | 0.05 Units/µL |

Screening Extract Libraries for Reduced 3' Primer Mismatch Extension Rate:

The extract library was screened by comparing the extension rate of a primer perfectly matched to an oligonucleotide template vs. the extension rate of a primer with a 3' G:T mismatch.

The enzyme extracts above were diluted 10-fold for primer extension reactions by combining 2.5 µl extract with 22.5 µl of a buffer containing 20 mM Tris-HCl, pH 8, 100 mM KCl, 0.1 mM EDTA, and 0.2% Tween-20 in a 384-well thermocycler plate, covering and heating for 10 minutes at 90° C. Control reactions with perfect match primer combined 0.5 µl of the diluted extract with 15 µl master mix in 384-well PCR plates. Extension of the primed template was monitored every 10 seconds in a modified kinetic thermal cycler using a CCD camera (see, Watson, supra). Master mix contained 50 nM primed primer template, 25 mM Tricine, pH 8.3, 100 mM KOAc, 0.6×SYBR Green I, 200 µM each dNTP, 100 nM Aptamer, and 2.5 mM Magnesium Acetate. In order to distinguish extension-derived fluorescence from background fluorescence, parallel wells were included in the experiment in which primer strand extension was prevented by leaving out the nucleotides from the reaction master mix. Reactions with the 3'-mismatched primer were performed as above except 1.5 µl of the diluted extract was added to each reaction and 1.5 mM Manganese Acetate was substituted for the Magnesium Acetate. Increasing the amount of extract three fold and using Manganese as the metal activator both make mismatch extension more likely and therefore improve the selectivity of the screen for those enzymes with the greatest ability to discriminate against 3'-mismatch extension.

Approximately 5000 mutant extracts were screened using the above protocol. Approximately 7% of the original pool was chosen for rescreening based on a perfect match primer extension value above an arbitrary cutoff and low mismatch to perfect match extension ratio. Culture wells corresponding to the top extracts were sampled to fresh growth medium and re-grown to produce a new culture plates containing the best mutants, as well as a number of parental cultures to be used for comparison. These culture plates were then used to make fresh extracts which were rescreened to confirm the original screen phenotype. The primer extension rates for the reactions with the perfect 3'-matched and the 3'-mismatched primers were calculated as the slope of the rise in fluorescence over time for the linear portion of the curve. The ratio of mismatched extension slope divided by the perfect matched extension slope was used to rank and select the best candidates. Selected clones from the rescreening, plus for comparison the parental clone Z05 D580G, with their respective genotypes and phenotypes are included in the table below.

TABLE 4

| Enzyme | Perfect Match Slope | Mismatch Slope | MM Slope/PM Slope |
|---|---|---|---|
| Z05 D580G | 8.29 | 8.04 | 0.97 |
| Z05 D580G R730C | 14.50 | 1.18 | 0.08 |

Example 2: Amplification of Mutant BRAF Plasmid Template in a Background of Wild-Type BRAF Human Genomic Template The effect of various substitutions at the R730 position of Z05 DNA polymerase on mismatch discrimination in allele-specific PCR was examined. These substitutions were created in Z05 D580G DNA polymerase by cloning synthetic gene fragments into a plasmid vector and the expressed mutant enzymes were purified and quantified. Z05 D580G mutants A (Alanine), D (Aspartic Acid), G (Glycine), and N (Asparagine) were compared to their parental enzyme in an allele-specific PCR assay.

The control DNA polymerase of this example is a Thermus sp. Z05 DNA polymerase of SEQ ID NO:1 except that the amino acid at position 580 is Glycine (e.g., a D580G substitution) (hereinafter Z05 D580G polymerase).

Primers were used that amplify a region of the human BRAF gene and are perfectly matched to the target when said target carries a mutation in codon 600 of BRAF, V600K. Against wild-type BRAF target, present in human genomic DNA, the allele selective primer results in a single A:C mismatch at the 3' end. The common primer is perfectly matched to the BRAF gene, as is the probe sequence, which allows for real-time, TaqMan detection of amplification. Each reaction had 10,000 copies (33 ng) of wild-type Human Genomic cell line DNA, or either 10,000 or 100 copies of a linearized plasmid containing the BRAF V600R mutant sequence in a final volume of 16 µl. To allow for the different salt optima of the enzymes, amplifications were performed using a range of KCl concentrations from 25 to 130 mM. Buffer conditions were 50 mM Tris-HCl pH 8.0, 2.5 mM MgCl$_2$, 0.2 mM each dNTP, 0.02 U/µl UNG, and 200 nM Aptamer. Forward and Reverse primers were at 100 nM and the probe was at 25 nM. All DNA polymerases were assayed at 20 nM and add 2% (v/v) enzyme storage buffer (50% v/v glycerol, 100 mM KCl, 20 mM Tris pH 8.0, 0.1 mM EDTA, 1 mM DTT, 0.5% Tween 20) to the reactions. The reactions were performed in a Roche LightCycler 480 thermal cycler and denatured using a temperature of 95° C. for 60 seconds, then 99 cycles of amplification were performed, using a denaturation temperature of 92° C. for 10 seconds and an annealing temperature of 62° C. for 30 seconds.

Reactions were in duplicate, crossing points ("Cps") were calculated by the Abs Quant/$2^{nd}$ derivative Max method and the Cps were averaged. PCR efficiency was calculated from the slope of the 100 and 10,000 copy perfect match plasmid reactions at the KCl concentration which resulted in the earliest 10,000 copy perfect match plasmid Cp. High Copy delta Cp is equal to the difference between the Cp values of the reactions with 10,000 copy of 3'-mismatched wild-type genomic target and the Cp values of the reactions with 10,000 copy of perfect match plasmid target.

The table below contains the averaged Cp values at the KCl concentration for each enzyme which resulted in the earliest high copy plasmid Cp and the calculated PCR efficiency and high copy delta Cp. Z05 D580G R730C DNA polymerase, which was identified in the initial mutant screen as described above, is included for reference. The data indicate that several amino acid substitutions at position R730 of Z05 DNA polymerase result in improved discrimination of primer mismatches in allele-selective PCR.

TABLE 5
Cps of Amplification of BRAF V600K mutant plasmid vs. Human genomic DNA

| Enzyme | 100 copies mutant plasmid | 10,000 copies mutant plasmid | 10,000 copies human gDNA | KCl Optimum | PCR Efficiency | High Copy delta Cp |
|---|---|---|---|---|---|---|
| Z05 D580G* | 31.2 | 24.3 | 26.3 | 115 | 96.3 | 2.0 |
| Z05 D580G R730A | 35.2 | 27.8 | 36.1 | 70 | 85.6 | 8.3 |
| Z05 D580G R730C | 35.9 | 28.2 | 37.2 | 70 | 81.4 | 9.0 |
| Z05 D580G R730D | 43.7 | 35.0 | 43.6 | 40 | 69.7 | 8.6 |
| Z05 D580G R730G | 38.1 | 30.1 | 39.9 | 55 | 78.2 | 9.8 |
| Z05 D580G R730N | 35.6 | 28.1 | 37.7 | 70 | 84.7 | 9.6 |

*Average of 4 experiments

This example demonstrates that the R730A, R730C, R730D, R730G, and R730N mutant enzymes have improved rare allele detection relative to the control parental enzyme, Z05 D580G.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

---

What is claimed is:

1. A method for conducting primer extension, comprising:
contacting a DNA polymerase with a primer, a polynucleotide template, and nucleoside triphosphates under conditions suitable for extension of the primer, thereby producing an extended primer,
wherein the DNA polymerase comprises a motif in the polymerase domain comprising G-Y-V-E-T-L-F-G-R-R-X5-Y-V-P, wherein:
X5 is any amino acid other than R (SEQ ID NO:10);
wherein the DNA polymerase has at least 90% sequence identity to the amino acid sequence of SEQ ID NOS: 1, 3, 4, 5, 6, or 7.

2. The method of claim 1, wherein the primer extension method is a method for conducting polymerase chain reaction (PCR), isothermal extension, or sequencing reactions.

3. The method of claim 1, wherein the polynucleotide template is DNA.

4. The method of claim 1, wherein the polynucleotide template is RNA.

5. The method of claim 1, wherein the conditions suitable for extension comprise Mg++ and Mn++.

6. The method of claim 1, wherein the nucleoside triphosphates comprise unconventional nucleotides, ribonucleotides and/or labeled nucleotides.

7. The method of claim 1, which is a method for polynucleotide amplification comprising contacting the DNA polymerase with a primer pair, the polynucleotide template, and the nucleoside triphosphates under conditions suitable for amplification of the polynucleotide.

8. The method of claim 1, wherein the primer extension method is a method for conducting reverse transcription polymerase chain reaction (RT-PCR).

9. The method of claim 1, wherein the primer and/or template comprises one or more nucleotide analogs.

10. The method of claim 1, wherein X5 is A, C, D, G, or N.

11. The method of claim 1, wherein the amino acid corresponding to position 580 of SEQ ID NO:1 is any amino acid other than D or E.

12. The method of claim 11, wherein the amino acid corresponding to position 580 of SEQ ID NO:1 is selected from the group consisting of L, G, T, Q, A, S, N, R, and K.

13. The method of claim 11, wherein the amino acid corresponding to position 580 of SEQ ID NO:1 is G.

14. The method of claim 1, wherein the DNA polymerase has at least 95% sequence identity to the amino acid sequence of SEQ ID NO:1.

15. The method of claim 1, wherein the DNA polymerase further comprises a motif comprising
T-G-R-L-S-S-X7-X8-P-N-L-Q-N; wherein
X7 is S or T; and
X8 is any amino acid other than D or E (SEQ ID NO:27).

16. The method of claim 15, wherein the amino acid of the DNA polymerase corresponding to position X8 is selected from the group consisting of L, G, T, Q, A, S, N, R, and K.

17. The method of claim 16, wherein the amino acid of the DNA polymerase corresponding to position X8 is G.

18. A method for conducting primer extension, comprising:
contacting a DNA polymerase with a primer, a polynucleotide template, and nucleoside triphosphates under conditions suitable for extension of the primer, thereby producing an extended primer,
wherein the DNA polymerase has increased 3'-mismatch discrimination activity compared with a control DNA polymerase, wherein the amino acid of the DNA polymerase corresponding to position 730 of SEQ ID NO:1 is any amino acid other than R,
wherein the DNA polymerase has at least 90% sequence identity to the amino acid sequence of SEQ ID NO:1, and wherein the control DNA polymerase has the same amino acid sequence as the DNA polymerase except that the amino acid of the control DNA polymerase corresponding to position 730 of SEQ ID NO:1 is R.

19. The method of claim 18, wherein the amino acid of the DNA polymerase corresponding to position 730 of SEQ ID NO:1 is A, C, D, G, or N.

20. The method of claim 18, wherein the DNA polymerase has at least 95% sequence identity to the amino acid sequence of SEQ ID NO:1.

* * * * *

SEQUENCE LISTING

```
<160> NUMBER OF SEQ ID NOS: 42

<210> SEQ ID NO 1
<211> LENGTH: 834
<212> TYPE: PRT
<213> ORGANISM: Thermus sp.
<220> FEATURE:
<223> OTHER INFORMATION: Thermus sp. Z05 DNA polymerase (Z05)

<400> SEQUENCE: 1

Met Lys Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175
```

```
Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
            245                 250                 255

Glu Val Asp Phe Ala Arg Arg Glu Pro Asp Arg Glu Gly Leu Arg
        260                 265                 270

Ala Phe Leu Glu Arg Leu Glu Phe Gly Ser Leu Leu His Glu Phe Gly
    275                 280                 285

Leu Leu Glu Ala Pro Ala Pro Leu Glu Glu Ala Pro Trp Pro Pro Pro
        290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
            325                 330                 335

Ala Lys Asp Pro Leu Ala Gly Leu Lys Asp Leu Lys Glu Val Arg Gly
        340                 345                 350

Leu Leu Ala Lys Asp Leu Ala Val Leu Ala Leu Arg Glu Gly Leu Asp
            355                 360                 365

Leu Ala Pro Ser Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
            405                 410                 415

Asn Leu Leu Glu Arg Leu Lys Gly Glu Glu Lys Leu Leu Trp Leu Tyr
        420                 425                 430

Gln Glu Val Glu Lys Pro Leu Ser Arg Val Leu Ala His Met Glu Ala
    435                 440                 445

Thr Gly Val Arg Leu Asp Val Ala Tyr Leu Lys Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
        500                 505                 510

Lys Arg Ser Thr Ser Ala Ala Val Leu Glu Ala Leu Arg Glu Ala His
    515                 520                 525

Pro Ile Val Glu Lys Ile Leu Gln His Arg Glu Leu Thr Lys Leu Lys
    530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Ile Arg Thr Pro Leu
        580                 585                 590

Gly Gln Arg Ile Arg Arg Ala Phe Val Ala Glu Ala Gly Trp Ala Leu
```

```
                595                 600                 605
Val Ala Leu Asp Tyr Ser Gln Ile Glu Leu Arg Val Leu Ala His Leu
    610                 615                 620

Ser Gly Asp Glu Asn Leu Ile Arg Val Phe Gln Gly Lys Asp Ile
625                 630                 635                 640

His Thr Gln Thr Ala Ser Trp Met Phe Gly Val Ser Pro Glu Ala Val
                    645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                    725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro His Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                    805                 810                 815

Val Pro Leu Glu Val Glu Val Gly Ile Gly Glu Asp Trp Leu Ser Ala
                820                 825                 830

Lys Gly

<210> SEQ ID NO 2
<211> LENGTH: 832
<212> TYPE: PRT
<213> ORGANISM: Thermus aquaticus
<220> FEATURE:
<223> OTHER INFORMATION: Thermus equaticus DNA polymerase (Taq)

<400> SEQUENCE: 2

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

```
Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 830
<212> TYPE: PRT
<213> ORGANISM: Thermus filiformis
<220> FEATURE:
<223> OTHER INFORMATION: Thermus filiformis DNA polymerase (Tfi)

<400> SEQUENCE: 3

Met Leu Pro Leu Leu Glu Pro Lys Gly Arg Val Leu Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Glu Val Ala Ile Val Val Phe Asp
    50                  55                  60

Ala Lys Ala Pro Ser Phe Arg His Glu Ala Tyr Glu Ala Tyr Lys Ala
65                  70                  75                  80

-continued

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
            100                 105                 110

Phe Glu Ala Asp Asp Val Leu Ala Thr Leu Ala Arg Lys Ala Glu Arg
            115                 120                 125

Glu Gly Tyr Glu Val Arg Ile Leu Ser Ala Asp Arg Asp Leu Tyr Gln
            130                 135                 140

Leu Leu Ser Asp Arg Ile His Leu Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175

Val Glu Tyr Arg Ala Leu Val Gly Asp Pro Ser Asp Asn Leu Pro Gly
            180                 185                 190

Val Pro Gly Ile Gly Glu Lys Thr Ala Leu Lys Leu Leu Lys Glu Trp
            195                 200                 205

Gly Ser Leu Glu Ala Ile Leu Lys Asn Leu Asp Gln Val Lys Pro Glu
            210                 215                 220

Arg Val Trp Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Thr Gly Lys Gly Leu Lys Ala Phe Leu Glu
            260                 265                 270

Arg Leu Glu Phe Gly Ser Leu Leu His Glu Phe Gly Leu Leu Glu Ala
            275                 280                 285

Pro Lys Glu Ala Glu Glu Ala Pro Trp Pro Pro Pro Gly Gly Ala Phe
            290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                325                 330                 335

Val Gly Ala Leu Lys Asp Leu Lys Glu Ile Arg Gly Leu Leu Ala Lys
            340                 345                 350

Asp Leu Ser Val Leu Ala Leu Arg Glu Gly Arg Glu Ile Pro Pro Gly
            355                 360                 365

Asp Asp Pro Met Leu Leu Ala Tyr Leu Leu Asp Pro Gly Asn Thr Asn
            370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
                405                 410                 415

Arg Val Ala Glu Glu Glu Arg Leu Leu Trp Leu Tyr Arg Glu Val Glu
            420                 425                 430

Arg Pro Leu Ala Gln Val Leu Ala His Met Glu Ala Thr Gly Val Arg
            435                 440                 445

Leu Asp Val Pro Tyr Leu Glu Ala Leu Ser Gln Glu Val Ala Phe Glu
450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr

```
                        500             505             510
    Ser Ala Val Leu Glu Leu Arg Glu His Pro Ile Val Gly
        515             520             525

Arg Ile Leu Glu Tyr Arg Glu Leu Met Lys Leu Lys Ser Thr Tyr Ile
        530             535             540

Asp Pro Leu Pro Arg Leu Val His Pro Lys Thr Gly Arg Leu His Thr
    545             550             555             560

Arg Phe Asn Gln Thr Ala Thr Ala Thr Gly Arg Leu Ser Ser Ser Asp
                565             570             575

Pro Asn Leu Gln Asn Ile Pro Val Arg Thr Pro Leu Gly Gln Arg Ile
                580             585             590

Arg Lys Ala Phe Ile Ala Glu Glu Gly His Leu Leu Val Ala Leu Asp
                595             600             605

Tyr Ser Gln Ile Glu Leu Arg Val Leu Ala His Leu Ser Gly Asp Glu
                610             615             620

Asn Leu Ile Arg Val Phe Arg Glu Gly Lys Asp Ile His Thr Glu Thr
    625             630             635             640

Ala Ala Trp Met Phe Gly Val Pro Pro Glu Gly Val Asp Gly Ala Met
                        645             650             655

Arg Arg Ala Ala Lys Thr Val Asn Phe Gly Val Leu Tyr Gly Met Ser
                        660             665             670

Ala His Arg Leu Ser Gln Glu Leu Ser Ile Pro Tyr Glu Glu Ala Ala
                        675             680             685

Ala Phe Ile Glu Arg Tyr Phe Gln Ser Phe Pro Lys Val Arg Ala Trp
                690             695             700

Ile Ala Lys Thr Leu Glu Glu Gly Arg Lys Lys Gly Tyr Val Glu Thr
    705             710             715             720

Leu Phe Gly Arg Arg Arg Tyr Val Pro Asp Leu Asn Ala Arg Val Lys
                        725             730             735

Ser Val Arg Glu Ala Ala Glu Arg Met Ala Phe Asn Met Pro Val Gln
                        740             745             750

Gly Thr Ala Ala Asp Leu Met Lys Leu Ala Met Val Lys Leu Phe Pro
                        755             760             765

Arg Leu Arg Pro Leu Gly Val Arg Ile Leu Leu Gln Val His Asp Glu
        770             775             780

Leu Val Leu Glu Ala Pro Lys Ala Arg Ala Glu Glu Ala Ala Gln Leu
    785             790             795             800

Ala Lys Glu Thr Met Glu Gly Val Tyr Pro Leu Ser Val Pro Leu Glu
                        805             810             815

Val Glu Val Gly Met Gly Glu Asp Trp Leu Ser Ala Lys Glu
                        820             825             830

<210> SEQ ID NO 4
<211> LENGTH: 831
<212> TYPE: PRT
<213> ORGANISM: Thermus flavus
<220> FEATURE:
<223> OTHER INFORMATION: Thermus flavus DNA polymerase (Tfl)

<400> SEQUENCE: 4

Met Ala Met Leu Pro Leu Phe Glu Pro Lys Gly Arg Val Leu Leu Val
 1               5                  10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
```

```
                35                  40                  45
Ser Leu Leu Lys Ala Leu Lys Glu Asp Gly Asp Val Val Val Val
 50                  55                  60

Phe Asp Ala Lys Ala Pro Ser Phe Arg His Glu Ala Tyr Glu Ala Tyr
 65                  70                  75                  80

Lys Ala Gly Arg Ala Pro Thr Pro Glu Asp Phe Pro Arg Gln Leu Ala
                 85                  90                  95

Leu Ile Lys Glu Leu Val Asp Leu Leu Gly Leu Val Arg Leu Glu Val
                100                 105                 110

Pro Gly Phe Glu Ala Asp Asp Val Leu Ala Thr Leu Ala Lys Arg Ala
                115                 120                 125

Glu Lys Glu Gly Tyr Glu Val Arg Ile Leu Thr Ala Asp Arg Asp Leu
                130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
                180                 185                 190

Pro Gly Val Lys Gly Ile Gly Glu Lys Thr Ala Gln Arg Leu Ile Arg
195                 200                 205

Glu Trp Gly Ser Leu Glu Asn Leu Phe Gln His Leu Asp Gln Val Lys
210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Arg Thr Pro Asn Leu Glu Gly Leu Arg Ala Phe Leu
                260                 265                 270

Glu Arg Leu Glu Phe Gly Ser Leu Leu His Glu Phe Gly Leu Leu Glu
                275                 280                 285

Gly Pro Lys Ala Ala Glu Glu Ala Pro Trp Pro Pro Pro Glu Gly Ala
                290                 295                 300

Phe Leu Gly Phe Ser Phe Ser Arg Pro Glu Pro Met Trp Ala Glu Leu
305                 310                 315                 320

Leu Ala Leu Ala Gly Ala Trp Glu Gly Arg Leu His Arg Ala Gln Asp
                325                 330                 335

Pro Leu Arg Gly Leu Arg Asp Leu Lys Gly Val Arg Gly Ile Leu Ala
                340                 345                 350

Lys Asp Leu Ala Val Leu Ala Leu Arg Glu Gly Leu Asp Leu Phe Pro
                355                 360                 365

Glu Asp Asp Pro Met Leu Leu Ala Tyr Leu Leu Asp Pro Ser Asn Thr
                370                 375                 380

Thr Pro Glu Gly Val Ala Arg Arg Tyr Gly Gly Glu Trp Thr Glu Asp
385                 390                 395                 400

Ala Gly Glu Arg Ala Leu Leu Ala Glu Arg Leu Phe Gln Thr Leu Lys
                405                 410                 415

Glu Arg Leu Lys Gly Glu Glu Arg Leu Leu Trp Leu Tyr Glu Glu Val
                420                 425                 430

Glu Lys Pro Leu Ser Arg Val Leu Ala Arg Met Glu Ala Thr Gly Val
                435                 440                 445

Arg Leu Asp Val Ala Tyr Leu Gln Ala Leu Ser Leu Glu Val Glu Ala
                450                 455                 460
```

Glu Val Arg Gln Leu Glu Glu Val Phe Arg Leu Ala Gly His Pro
465                 470                 475                 480

Phe Asn Leu Asn Ser Arg Asp Gln Leu Glu Arg Val Leu Phe Asp Glu
                485                 490                 495

Leu Gly Leu Pro Ala Ile Gly Lys Thr Glu Lys Thr Gly Lys Arg Ser
            500                 505                 510

Thr Ser Ala Ala Val Leu Glu Ala Leu Arg Glu Ala His Pro Ile Val
        515                 520                 525

Asp Arg Ile Leu Gln Tyr Arg Glu Leu Thr Lys Leu Lys Asn Thr Tyr
530                 535                 540

Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
            580                 585                 590

Ile Arg Arg Ala Phe Val Ala Glu Glu Gly Trp Val Leu Val Val Leu
        595                 600                 605

Asp Tyr Ser Gln Ile Glu Leu Arg Val Leu Ala His Leu Ser Gly Asp
610                 615                 620

Glu Asn Leu Ile Arg Val Phe Gln Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
            660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
        690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
        770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Glu Asp Trp Leu Ser Ala Lys Glu
            820                 825                 830

<210> SEQ ID NO 5
<211> LENGTH: 830
<212> TYPE: PRT
<213> ORGANISM: Thermus sp.
<220> FEATURE:
<223> OTHER INFORMATION: Thermus sp. sps17 DNA polymerase (Sps17)

<400> SEQUENCE: 5

-continued

```
Met Leu Pro Leu Phe Glu Pro Lys Gly Arg Val Leu Val Asp Gly
 1               5                  10                  15

His His Leu Ala Tyr Arg Thr Phe Ala Leu Lys Gly Leu Thr Thr
             20                  25                  30

Ser Arg Gly Glu Pro Val Gln Ala Val Tyr Gly Phe Ala Lys Ser Leu
         35                  40                  45

Leu Lys Ala Leu Lys Glu Asp Gly Glu Val Ala Ile Val Val Phe Asp
     50                  55                  60

Ala Lys Ala Pro Ser Phe Arg His Glu Ala Tyr Glu Ala Tyr Lys Ala
 65                  70                  75                  80

Gly Arg Ala Pro Thr Pro Glu Asp Phe Pro Arg Gln Leu Ala Leu Ile
                 85                  90                  95

Lys Glu Leu Val Asp Leu Leu Gly Leu Val Arg Leu Glu Val Pro Gly
             100                 105                 110

Phe Glu Ala Asp Asp Val Leu Ala Thr Leu Ala Lys Lys Ala Glu Arg
         115                 120                 125

Glu Gly Tyr Glu Val Arg Ile Leu Ser Ala Asp Arg Asp Leu Tyr Gln
130                 135                 140

Leu Leu Ser Asp Arg Ile His Leu Leu His Pro Glu Gly Glu Val Leu
145                 150                 155                 160

Thr Pro Gly Trp Leu Gln Glu Arg Tyr Gly Leu Ser Pro Glu Arg Trp
                 165                 170                 175

Val Glu Tyr Arg Ala Leu Val Gly Asp Pro Ser Asp Asn Leu Pro Gly
             180                 185                 190

Val Pro Gly Ile Gly Glu Lys Thr Ala Leu Lys Leu Leu Lys Glu Trp
         195                 200                 205

Gly Ser Leu Glu Ala Ile Leu Lys Asn Leu Asp Gln Val Lys Pro Glu
210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                 245                 250                 255

Ala Lys Arg Arg Glu Pro Asp Trp Glu Gly Leu Lys Ala Phe Leu Glu
             260                 265                 270

Arg Leu Glu Phe Gly Ser Leu Leu His Glu Phe Gly Leu Leu Glu Ala
         275                 280                 285

Pro Lys Glu Ala Glu Glu Ala Pro Trp Pro Pro Gly Gly Ala Phe
290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                 325                 330                 335

Val Gly Ala Leu Lys Asp Leu Lys Glu Ile Arg Gly Leu Leu Ala Lys
             340                 345                 350

Asp Leu Ser Val Leu Ala Leu Arg Glu Gly Arg Glu Ile Pro Pro Gly
         355                 360                 365

Asp Asp Pro Met Leu Leu Ala Tyr Leu Leu Asp Pro Gly Asn Thr Asn
370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
                 405                 410                 415
```

```
Arg Val Ala Glu Glu Arg Leu Leu Trp Leu Tyr Arg Glu Val Glu
            420                 425                 430

Arg Pro Leu Ala Gln Val Leu Ala His Met Glu Ala Thr Gly Val Arg
        435                 440                 445

Leu Asp Val Pro Tyr Leu Glu Ala Leu Ser Gln Glu Val Ala Phe Glu
    450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Leu Leu Arg Glu Ala His Pro Ile Val Gly
        515                 520                 525

Arg Ile Leu Glu Tyr Arg Glu Leu Met Lys Leu Lys Ser Thr Tyr Ile
    530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Lys Ala Phe Ile Ala Glu Gly His Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Arg Glu Gly Lys Asp Ile His Thr Glu Thr
625                 630                 635                 640

Ala Ala Trp Met Phe Gly Val Pro Pro Glu Gly Val Asp Gly Ala Met
                645                 650                 655

Arg Arg Ala Ala Lys Thr Val Asn Phe Gly Val Leu Tyr Gly Met Ser
            660                 665                 670

Ala His Arg Leu Ser Gln Glu Leu Ser Ile Pro Tyr Glu Glu Ala Ala
        675                 680                 685

Ala Phe Ile Glu Arg Tyr Phe Gln Ser Phe Pro Lys Val Arg Ala Trp
    690                 695                 700

Ile Ala Lys Thr Leu Glu Glu Gly Arg Lys Lys Gly Tyr Val Glu Thr
705                 710                 715                 720

Leu Phe Gly Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Asp Leu Met Lys Leu Ala Met Val Lys Leu Phe Pro
        755                 760                 765

Arg Leu Arg Pro Leu Gly Val Arg Ile Leu Leu Gln Val His Asp Glu
    770                 775                 780

Leu Val Leu Glu Ala Pro Lys Ala Arg Ala Glu Glu Ala Ala Gln Leu
785                 790                 795                 800

Ala Lys Glu Thr Met Glu Gly Val Tyr Pro Leu Ser Val Pro Leu Glu
                805                 810                 815

Val Glu Val Gly Met Gly Glu Asp Trp Leu Ser Ala Lys Ala
            820                 825                 830
```

```
<210> SEQ ID NO 6
<211> LENGTH: 834
<212> TYPE: PRT
<213> ORGANISM: Thermus thermophilus
<220> FEATURE:
<223> OTHER INFORMATION: Thermus thermophilus DNA polymerase (Tth)

<400> SEQUENCE: 6

Met Glu Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
                 20                  25                  30

Leu Thr Thr Ser Arg Gly Glu Pro Val Gln Ala Val Tyr Gly Phe Ala
             35                  40                  45

Lys Ser Leu Leu Lys Ala Leu Lys Glu Asp Gly Tyr Lys Ala Val Phe
         50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
```

```
            370                 375                 380
Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Arg Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Lys Arg Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800
```

-continued

```
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly

<210> SEQ ID NO 7
<211> LENGTH: 834
<212> TYPE: PRT
<213> ORGANISM: Thermus caldophilus
<220> FEATURE:
<223> OTHER INFORMATION: Thermus caldophilus DNA polymerase (Tca)

<400> SEQUENCE: 7

Met Glu Ala Met Leu Pro Leu Phe Glu Pro Lys Gly Arg Val Leu Leu
  1               5                  10                  15
Val Asp Gly His His Leu Ala Tyr Arg Thr Phe Phe Ala Leu Lys Gly
                 20                  25                  30
Leu Thr Thr Ser Arg Gly Glu Pro Val Gln Ala Val Tyr Gly Phe Ala
             35                  40                  45
Lys Ser Leu Leu Lys Ala Leu Lys Glu Asp Gly Tyr Lys Ala Val Phe
 50                  55                  60
Val Val Phe Asp Ala Lys Ala Pro Ser Phe Arg His Glu Ala Tyr Glu
 65                  70                  75                  80
Ala Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Phe Thr Arg Leu
            100                 105                 110
Glu Val Pro Gly Tyr Glu Ala Asp Asp Val Leu Ala Thr Leu Ala Lys
            115                 120                 125
Asn Pro Glu Lys Glu Gly Tyr Glu Val Arg Ile Leu Thr Ala Asp Arg
130                 135                 140
Asp Leu Asp Gln Leu Val Ser Asp Arg Val Ala Val Leu His Pro Glu
145                 150                 155                 160
Gly His Leu Ile Thr Pro Glu Trp Leu Trp Gln Lys Tyr Gly Leu Lys
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
            195                 200                 205
Leu Lys Glu Trp Gly Ser Leu Glu Asn Leu Leu Lys Asn Leu Asp Arg
        210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
            275                 280                 285
Leu Leu Glu Ala Pro Ala Pro Leu Glu Glu Ala Pro Trp Pro Pro Pro
        290                 295                 300
Glu Gly Ala Phe Val Gly Phe Val Leu Ser Arg Pro Glu Pro Met Trp
305                 310                 315                 320
```

-continued

```
Ala Glu Leu Lys Ala Leu Ala Cys Arg Asp Gly Arg Val His Arg
            325                 330                 335

Ala Ala Asp Pro Leu Ala Gly Leu Lys Asp Leu Lys Glu Val Arg Gly
        340                 345                 350

Leu Leu Ala Lys Asp Leu Ala Val Leu Ala Ser Arg Glu Gly Leu Asp
            355                 360                 365

Leu Val Pro Gly Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
```

```
                    740                 745                 750
Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
        770                 775                 780

Val His Asp Glu Leu Leu Leu Glu Ala Pro Gln Ala Gly Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 8
<211> LENGTH: 14
<212> TYPE: PRT
<213> ORGANISM: Artificial Sequence
<220> FEATURE:
<223> OTHER INFORMATION: synthetic DNA polymerase domain motif
<220> FEATURE:
<221> NAME/KEY: VARIANT
<222> LOCATION: (4)...(4)
<223> OTHER INFORMATION: Xaa = Glu, Arg or Thr
<220> FEATURE:
<221> NAME/KEY: VARIANT
<222> LOCATION: (7)...(7)
<223> OTHER INFORMATION: Xaa = Phe, Tyr or Leu
<220> FEATURE:
<221> NAME/KEY: VARIANT
<222> LOCATION: (8)...(8)
<223> OTHER INFORMATION: Xaa = Gly or His
<220> FEATURE:
<221> NAME/KEY: VARIANT
<222> LOCATION: (10)...(10)
<223> OTHER INFORMATION: Xaa = Arg or Lys
<220> FEATURE:
<221> NAME/KEY: VARIANT
<222> LOCATION: (11)...(11)
<223> OTHER INFORMATION: Xaa = any amino acid other than Arg
<220> FEATURE:
<221> NAME/KEY: VARIANT
<222> LOCATION: (12)...(12)
<223> OTHER INFORMATION: Xaa = Tyr or Asp
<220> FEATURE:
<221> NAME/KEY: VARIANT
<222> LOCATION: (13)...(13)
<223> OTHER INFORMATION: Xaa = Val, Ile or Leu

<400> SEQUENCE: 8

Gly Tyr Val Xaa Thr Leu Xaa Xaa Arg Xaa Xaa Xaa Xaa Pro
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: synthetic DNA polymerase domain motif
<220> FEATURE:
<221> NAME/KEY: VARIANT
<222> LOCATION: (4)...(4)
<223> OTHER INFORMATION: Xaa = Glu or Arg
<220> FEATURE:
<221> NAME/KEY: VARIANT
<222> LOCATION: (10)...(10)
<223> OTHER INFORMATION: Xaa = Arg or Lys
<220> FEATURE:
<221> NAME/KEY: VARIANT
<222> LOCATION: (11)...(11)
<223> OTHER INFORMATION: Xaa = any amino acid other than Arg
```

```
<220> FEATURE:
<221> NAME/KEY: VARIANT
<222> LOCATION: (12)...(12)
<223> OTHER INFORMATION: Xaa = Tyr or Asp
<220> FEATURE:
<221> NAME/KEY: VARIANT
<222> LOCATION: (13)...(13)
<223> OTHER INFORMATION: Xaa = Val or Ile

<400> SEQUENCE: 9

Gly Tyr Val Xaa Thr Leu Phe Gly Arg Xaa Xaa Xaa Xaa Pro
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: synthetic DNA polymerase domain motif
<220> FEATURE:
<221> NAME/KEY: VARIANT
<222> LOCATION: (11)...(11)
<223> OTHER INFORMATION: Xaa = any amino acid other than Arg

<400> SEQUENCE: 10

Gly Tyr Val Glu Thr Leu Phe Gly Arg Arg Xaa Tyr Val Pro
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: synthetic DNA polymerase domain motif
<220> FEATURE:
<221> NAME/KEY: VARIANT
<222> LOCATION: (11)...(11)
<223> OTHER INFORMATION: Xaa = Ala, Cys, Asp, Gly or Asn

<400> SEQUENCE: 11

Gly Tyr Val Glu Thr Leu Phe Gly Arg Arg Xaa Tyr Val Pro
 1               5                  10

<210> SEQ ID NO 12
<211> LENGTH: 34
<212> TYPE: PRT
<213> ORGANISM: Artificial Sequence
<220> FEATURE:
<223> OTHER INFORMATION: synthetic region from polymerase domain of
      Thermus sp. Z05 DNA polymerase (Z05)

<400> SEQUENCE: 12

Ala Trp Ile Glu Lys Thr Leu Glu Glu Gly Arg Lys Arg Gly Tyr Val
 1               5                  10                  15

Glu Thr Leu Phe Gly Arg Arg Arg Tyr Val Pro Asp Leu Asn Ala Arg
            20                  25                  30

Val Lys

<210> SEQ ID NO 13
<211> LENGTH: 34
<212> TYPE: PRT
<213> ORGANISM: Artificial Sequence
<220> FEATURE:
<223> OTHER INFORMATION: synthetic region from polymerase domain of
      Thermus aquaticus DNA polymerase (Taq)

<400> SEQUENCE: 13

Ala Trp Ile Glu Lys Thr Leu Glu Glu Gly Arg Arg Arg Gly Tyr Val
```

```
                1               5                   10                  15
Glu Thr Leu Phe Gly Arg Arg Arg Tyr Val Pro Asp Leu Glu Ala Arg
            20                  25                  30

Val Lys

<210> SEQ ID NO 14
<211> LENGTH: 34
<212> TYPE: PRT
<213> ORGANISM: Artificial Sequence
<220> FEATURE:
<223> OTHER INFORMATION: synthetic region from polymerase domain of
      Thermus filiformus DNA polymerase (Tfi)

<400> SEQUENCE: 14

Ala Trp Ile Ala Lys Thr Leu Glu Glu Gly Arg Lys Lys Gly Tyr Val
1               5                   10                  15

Glu Thr Leu Phe Gly Arg Arg Arg Tyr Val Pro Asp Leu Asn Ala Arg
            20                  25                  30

Val Lys

<210> SEQ ID NO 15
<211> LENGTH: 34
<212> TYPE: PRT
<213> ORGANISM: Artificial Sequence
<220> FEATURE:
<223> OTHER INFORMATION: synthetic region from polymerase domain of
      Thermus flavus DNA polymerase (Tfl)

<400> SEQUENCE: 15

Ala Trp Ile Glu Gly Thr Leu Glu Glu Gly Arg Arg Arg Gly Tyr Val
1               5                   10                  15

Glu Thr Leu Phe Gly Arg Arg Arg Tyr Val Pro Asp Leu Asn Ala Arg
            20                  25                  30

Val Lys

<210> SEQ ID NO 16
<211> LENGTH: 34
<212> TYPE: PRT
<213> ORGANISM: Artificial Sequence
<220> FEATURE:
<223> OTHER INFORMATION: synthetic region from polymerase domain of
      Thermus sp. Sps17 DNA polymerase (Sps17)

<400> SEQUENCE: 16

Ala Trp Ile Ala Lys Thr Leu Glu Glu Gly Arg Lys Lys Gly Tyr Val
1               5                   10                  15

Glu Thr Leu Phe Gly Arg Arg Arg Tyr Val Pro Asp Leu Asn Ala Arg
            20                  25                  30

Val Lys

<210> SEQ ID NO 17
<211> LENGTH: 34
<212> TYPE: PRT
<213> ORGANISM: Artificial Sequence
<220> FEATURE:
<223> OTHER INFORMATION: synthetic region from polymerase domain of
      Thermus thermophilus DNA polymerase (Tth)

<400> SEQUENCE: 17

Ala Trp Ile Glu Lys Thr Leu Glu Glu Gly Arg Lys Arg Gly Tyr Val
1               5                   10                  15

Glu Thr Leu Phe Gly Arg Arg Arg Tyr Val Pro Asp Leu Asn Ala Arg
```

Val Lys

<210> SEQ ID NO 18
<211> LENGTH: 34
<212> TYPE: PRT
<213> ORGANISM: Artificial Sequence
<220> FEATURE:
<223> OTHER INFORMATION: synthetic region from polymerase domain of
      Thermus caldophilus DNA polymerase (Tca)

<400> SEQUENCE: 18

Ala Trp Ile Glu Lys Thr Leu Glu Glu Gly Arg Lys Arg Gly Tyr Val
 1               5                  10                  15

Glu Thr Leu Phe Gly Arg Arg Arg Tyr Val Pro Asp Leu Asn Ala Arg
            20                  25                  30

Val Lys

<210> SEQ ID NO 19
<211> LENGTH: 34
<212> TYPE: PRT
<213> ORGANISM: Artificial Sequence
<220> FEATURE:
<223> OTHER INFORMATION: synthetic region from polymerase domain of
      Thermotoga maritima DNA polymerase (Tma)

<400> SEQUENCE: 19

Asp Tyr Ile Gln Arg Val Val Ser Glu Ala Lys Glu Lys Gly Tyr Val
 1               5                  10                  15

Arg Thr Leu Phe Gly Arg Lys Arg Asp Ile Pro Gln Leu Met Ala Arg
            20                  25                  30

Asp Arg

<210> SEQ ID NO 20
<211> LENGTH: 34
<212> TYPE: PRT
<213> ORGANISM: Artificial Sequence
<220> FEATURE:
<223> OTHER INFORMATION: synthetic region from polymerase domain of
      Thermotoga neopolitana DNA polymerase (Tne)

<400> SEQUENCE: 20

Ser Tyr Ile Gln Gln Val Val Ala Glu Ala Lys Glu Lys Gly Tyr Val
 1               5                  10                  15

Arg Thr Leu Phe Gly Arg Lys Arg Asp Ile Pro Gln Leu Met Ala Arg
            20                  25                  30

Asp Lys

<210> SEQ ID NO 21
<211> LENGTH: 34
<212> TYPE: PRT
<213> ORGANISM: Artificial Sequence
<220> FEATURE:
<223> OTHER INFORMATION: synthetic region from polymerase domain of
      Thermosipho africanus DNA polymerase (Taf)

<400> SEQUENCE: 21

Glu Tyr Leu Lys Arg Met Lys Asp Glu Ala Arg Lys Lys Gly Tyr Val
 1               5                  10                  15

Thr Thr Leu Phe Gly Arg Arg Arg Tyr Ile Pro Gln Leu Arg Ser Lys
            20                  25                  30

Asn Gly

<210> SEQ ID NO 22

<400> SEQUENCE: 22

000

<210> SEQ ID NO 23
<211> LENGTH: 34
<212> TYPE: PRT
<213> ORGANISM: Artificial Sequence
<220> FEATURE:
<223> OTHER INFORMATION: synthetic region from polymerase domain of
      Deinococcus radiodurans DNA polymerase (Dra)

<400> SEQUENCE: 23

Arg Tyr Ile Asn His Thr Leu Asp Phe Gly Arg Thr His Gly Tyr Val
 1               5                  10                  15

Glu Thr Leu Tyr Gly Arg Arg Arg Tyr Val Pro Gly Leu Ser Ser Arg
             20                  25                  30

Asn Arg

<210> SEQ ID NO 24
<211> LENGTH: 34
<212> TYPE: PRT
<213> ORGANISM: Artificial Sequence
<220> FEATURE:
<223> OTHER INFORMATION: synthetic region from polymerase domain of
      Bacillus stearothermophilus DNA polymerase (Bst)

<400> SEQUENCE: 24

Gln Tyr Met Asp Asn Ile Val Gln Glu Ala Lys Gln Lys Gly Tyr Val
 1               5                  10                  15

Thr Thr Leu Leu His Arg Arg Arg Tyr Leu Pro Asp Ile Thr Ser Arg
             20                  25                  30

Asn Phe

<210> SEQ ID NO 25
<211> LENGTH: 34
<212> TYPE: PRT
<213> ORGANISM: Artificial Sequence
<220> FEATURE:
<223> OTHER INFORMATION: synthetic region from polymerase domain of
      Bacillus caldotenax DNA polymerase (Bca)

<400> SEQUENCE: 25

Arg Tyr Met Glu Asn Ile Val Gln Glu Ala Lys Gln Lys Gly Tyr Val
 1               5                  10                  15

Thr Thr Leu Leu His Arg Arg Arg Tyr Leu Pro Asp Ile Thr Ser Arg
             20                  25                  30

Asn Phe

<210> SEQ ID NO 26
<211> LENGTH: 14
<212> TYPE: PRT
<213> ORGANISM: Artificial Sequence
<220> FEATURE:
<223> OTHER INFORMATION: synthetic native consensus motif for region
      from polymerase domain of bacterial DNA polymerase
<220> FEATURE:
<221> NAME/KEY: VARIANT
<222> LOCATION: (4)...(4)
<223> OTHER INFORMATION: Xaa = Glu, Arg or Thr
<220> FEATURE:
<221> NAME/KEY: VARIANT

```
<222> LOCATION: (7)...(7)
<223> OTHER INFORMATION: Xaa = Phe, Tyr or Leu
<220> FEATURE:
<221> NAME/KEY: VARIANT
<222> LOCATION: (8)...(8)
<223> OTHER INFORMATION: Xaa = Gly or His
<220> FEATURE:
<221> NAME/KEY: VARIANT
<222> LOCATION: (10)...(10)
<223> OTHER INFORMATION: Xaa = Arg or Lys
<220> FEATURE:
<221> NAME/KEY: VARIANT
<222> LOCATION: (12)...(12)
<223> OTHER INFORMATION: Xaa = Tyr or Asp
<220> FEATURE:
<221> NAME/KEY: VARIANT
<222> LOCATION: (13)...(13)
<223> OTHER INFORMATION: Xaa = Val, Ile or Leu

<400> SEQUENCE: 26

Gly Tyr Val Xaa Thr Leu Xaa Xaa Arg Xaa Arg Xaa Xaa Pro
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: synthetic polymerase motif corresponding to the
      D580X mutation of Z05, modified Z05 D580 motif
<220> FEATURE:
<221> NAME/KEY: VARIANT
<222> LOCATION: (7)...(7)
<223> OTHER INFORMATION: Xaa = Ser or Thr
<220> FEATURE:
<221> NAME/KEY: VARIANT
<222> LOCATION: (8)...(8)
<223> OTHER INFORMATION: Xaa = any amino acid other than Asp or Glu

<400> SEQUENCE: 27

Thr Gly Arg Leu Ser Ser Xaa Xaa Pro Asn Leu Gln Asn
 1               5                  10

<210> SEQ ID NO 28
<211> LENGTH: 8
<212> TYPE: PRT
<213> ORGANISM: Artificial Sequence
<220> FEATURE:
<223> OTHER INFORMATION: synthetic conserved DNA polymerase active site
      motif A

<400> SEQUENCE: 28

Asp Tyr Ser Gln Ile Glu Leu Arg
 1               5

<210> SEQ ID NO 29
<211> LENGTH: 893
<212> TYPE: PRT
<213> ORGANISM: Artificial Sequence
<220> FEATURE:
<223> OTHER INFORMATION: synthetic chimeric CS5 DNA polymerase derived
      from N-terminal 5'-nuclease domain of Thermus sp. Z05
      and C-terminal 3'-5' exonuclease and polymerase
      domains of Thermotoga maritima DNA polymerases

<400> SEQUENCE: 29

Met Lys Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
             20                  25                  30
```

```
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Tyr Lys Ala Val Phe
 50                  55                  60
Val Val Phe Asp Ala Lys Ala Pro Ser Phe Arg His Glu Ala Tyr Glu
 65                  70                  75                  80
Ala Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Phe Thr Arg Leu
                100                 105                 110
Glu Val Pro Gly Phe Glu Ala Asp Asp Val Leu Ala Thr Leu Ala Lys
            115                 120                 125
Lys Ala Glu Arg Glu Gly Tyr Glu Val Arg Ile Leu Thr Ala Asp Arg
130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Lys
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
            195                 200                 205
Leu Lys Glu Trp Gly Ser Leu Glu Asn Ile Leu Lys Asn Leu Asp Arg
        210                 215                 220
Val Lys Pro Glu Ser Val Arg Glu Arg Ile Lys Ala His Leu Glu Asp
225                 230                 235                 240
Leu Lys Leu Ser Leu Glu Leu Ser Arg Val Arg Ser Asp Leu Pro Leu
                245                 250                 255
Glu Val Asp Phe Ala Arg Arg Arg Glu Pro Asp Arg Glu Gly Leu Arg
            260                 265                 270
Ala Phe Leu Glu Arg Leu Glu Phe Gly Ser Leu Leu His Glu Phe Gly
        275                 280                 285
Leu Leu Glu Glu Ser Glu Pro Val Gly Tyr Arg Ile Val Lys Asp Leu
    290                 295                 300
Val Glu Phe Glu Lys Leu Ile Glu Lys Leu Arg Glu Ser Pro Ser Phe
305                 310                 315                 320
Ala Ile Asp Leu Glu Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
        355                 360                 365
Lys Leu Lys Glu Ile Leu Glu Asp Pro Gly Ala Lys Ile Val Gly Gln
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
        435                 440                 445
Phe Gly Phe Ser Phe Ala Asp Val Pro Val Glu Lys Ala Ala Asn Tyr
```

```
                450                 455                 460
Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
                515                 520                 525

Leu Glu Glu Leu Ala Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
                595                 600                 605

Asp Ala Leu Pro Lys Met Val Asn Pro Lys Thr Gly Arg Ile His Ala
                610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
                675                 680                 685

Glu Asn Leu Leu Arg Ala Phe Glu Gly Ile Asp Val His Thr Leu
                690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
                755                 760                 765

Tyr Ile Gln Arg Val Val Ser Glu Ala Lys Glu Lys Gly Tyr Val Arg
                770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
                850                 855                 860

Val Glu Leu Val Lys Asp Arg Met Thr Asn Val Val Lys Leu Ser Val
865                 870                 875                 880
```

Pro Leu Glu Val Asp Val Thr Ile Gly Lys Thr Trp Ser
                885                 890

<210> SEQ ID NO 30
<211> LENGTH: 893
<212> TYPE: PRT
<213> ORGANISM: Artificial Sequence
<220> FEATURE:
<223> OTHER INFORMATION: synthetic chimeric CS6 DNA polymerase derived
      from N-terminal 5'-nuclease domain of Thermus sp. Z05
      and C-terminal 3'-5' exonuclease and polymerase
      domains of Thermotoga maritima DNA polymerases

<400> SEQUENCE: 30

Met Lys Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Ala Leu Ala Thr Ser Ser Leu Asp Pro Phe Asp Cys Asp Ile
                325                 330                 335

-continued

Val Gly Ile Ser Val Ser Phe Lys Pro Lys Glu Ala Tyr Tyr Ile Pro
        340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
        500                 505                 510

Val Asp Thr Glu Phe Leu Lys Lys Leu Ser Glu Tyr Gly Lys Lys
            515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
        580                 585                 590

Leu Ile Leu Glu Tyr Arg Lys Ile Gln Lys Leu Lys Ser Thr Tyr Ile
    595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
        660                 665                 670

Asp Tyr Ser Gln Ile Glu Leu Arg Ile Leu Ala His Leu Ser Gly Asp
    675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
                705                 710                 715                 720

Met Arg Arg Ala Gly Lys Met Val Asn Phe Ser Ile Ile Tyr Gly Val
        725                 730                 735

Thr Pro Tyr Gly Leu Ser Val Arg Leu Gly Val Pro Val Lys Glu Ala
            740                 745                 750

```
Glu Lys Met Ile Val Asn Tyr Phe Val Leu Tyr Pro Lys Val Arg Asp
            755                 760                 765
Tyr Ile Gln Arg Val Val Ser Glu Ala Lys Lys Gly Tyr Val Arg
    770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
                820                 825                 830
Arg Glu Leu Lys Glu Arg Lys Met Arg Ser Lys Met Ile Ile Gln Val
            835                 840                 845
His Asp Glu Leu Val Phe Glu Val Pro Asn Glu Glu Lys Asp Ala Leu
    850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890

<210> SEQ ID NO 31
<211> LENGTH: 21
<212> TYPE: DNA
<213> ORGANISM: Artificial Sequence
<220> FEATURE:
<223> OTHER INFORMATION: synthetic error-prone (mutagenic) PCR
      amplification forward primer

<400> SEQUENCE: 31
ctacctcctg daccccteca a                                           21

<210> SEQ ID NO 32
<211> LENGTH: 25
<212> TYPE: DNA
<213> ORGANISM: Artificial Sequence
<220> FEATURE:
<223> OTHER INFORMATION: synthetic error-prone (mutagenic) PCR
      amplification reverse primer

<400> SEQUENCE: 32
ataaccaact ggtagtggcg tgtaa                                       25

<210> SEQ ID NO 33
<211> LENGTH: 1491
<212> TYPE: DNA
<213> ORGANISM: Artificial Sequence
<220> FEATURE:
<223> OTHER INFORMATION: synthetic amplicon encoding polymerase domain
      of Z05 D580G DNA polymerase amplified by error-prone (mutagenic)
      PCR between BlpI and BglII restriction sites

<400> SEQUENCE: 33
ctacctcctg daccccteca acaccaccce cgaggggggtg gcccggcgct acggggggga        60
gtggacggag gacgccgccc accgggccct cctcgctgag cggctccagc aaaacctctt       120
ggaacgcctc aagggagagg aaaagctcct ttggctctac caagaggtgg aaaagcccct       180
ctcccgggtc ctggcccaca tggaggccac cgggggtaagg ctggacgtgg cctatctaaa      240 ggcccttttcc ctggagcttg cggaggagat cgccgcctc gaggaggagg tcttccgcct      300
ggcgggccac cccttcaacc tgaactcccg tgaccagcta gagcgggtgc tctttgacga      360
gcttaggctt cccgccctgg gcaagacgca aaagacgggg aagcgctcca ccagcgccgc      420
```

```
ggtgctggag gccctcaggg aggcccaccc catcgtggag aagatcctcc agcaccggga    480
gctcaccaag ctcaagaaca cctacgtaga ccccctcccg ggcctcgtcc acccgaggac    540
gggccgcctc cacacccgct tcaaccagac agccacggcc acgggaaggc tctctagctc    600
cgggcccaac ctgcagaaca tccccatccg caccccttg gccagagga tccgccgggc     660 cttcgtggcc gaggcgggat gggcgttggt ggccctggac tatagccaga tagagctccg    720
ggtcctcgcc cacctctccg gggacgagaa cctgatcagg gtcttccagg aggggaagga    780
catccacacc cagaccgcaa gctggatgtt cggcgtctcc ccggaggccg tggacccct    840 gatgcgccgg gcggccaaga cggtgaactt cggcgtcctc tacggcatgt ccgcccatag    900
gctctcccag gagcttgcca tccctacga ggaggcggtg gcctttatag agcgctactt    960
ccaaagcttc cccaaggtgc gggcctggat agaaaagacc ctggaggagg ggaggaagcg    1020
gggctacgtg gaaaccctct tcggaagaag gcgctacgtg cccgacctca cgcccgggt    1080 gaagagcgtc agggaggccg cggagcgcat ggccttcaac atgcccgtcc agggcaccgc    1140
cgccgacctc atgaagctcg ccatggtgaa gctcttcccc cacctccggg agatgggggc    1200
ccgcatgctc ctccaggtcc acgacgagct cctcctggag gccccccaag cgcgggccga    1260
ggaggtggcg gctttggcca aggaggccat ggagaaggcc tatcccctcg ccgtgcccct    1320
ggaggtggag gtggggatcg gggaggactg gctttccgcc aagggctgat atcagatctc    1380
cctgattatg cgtcagtcta tgaagaaaaa tcgtatacag atggacgaag agaatcct     1440 tgtgaattta acagagggta tagggattac acgccactac cagttggtta t            1491

<210> SEQ ID NO 34
<211> LENGTH: 110
<212> TYPE: DNA
<213> ORGANISM: Artificial Sequence
<220> FEATURE:
<223> OTHER INFORMATION: synthetic wild-type BRAF V600K target
      polynucleotide

<400> SEQUENCE: 34
agtaaaaata ggtgattttg gtctagctac agtgaaatct cgatggagtg ggtcccatca     60
gtttgaacag ttgtctggat ccattttgtg gatggtaaga attgaggcta                110

<210> SEQ ID NO 35
<211> LENGTH: 110
<212> TYPE: DNA
<213> ORGANISM: Artificial Sequence
<220> FEATURE:
<223> OTHER INFORMATION: synthetic mutant BRAF V600R target
      polynucleotide

<400> SEQUENCE: 35
agtaaaaata ggtgattttg gtctagctac aaggaaatct cgatggagtg ggtcccatca     60
gtttgaacag ttgtctggat ccattttgtg gatggtaaga attgaggcta                110

<210> SEQ ID NO 36
<211> LENGTH: 921
<212> TYPE: PRT
<213> ORGANISM: Deinococcus radiodurans
<220> FEATURE:
<223> OTHER INFORMATION: Deinococcus radiodurans DNA polymerase (Dra)

<400> SEQUENCE: 36

Met Ala Asp Ala Ser Pro Asp Pro Ser Lys Pro Asp Ala Leu Val Leu
1               5                   10                  15
```

```
Ile Asp Gly His Ala Leu Ala Phe Arg Ser Tyr Phe Ala Leu Pro Pro
             20                  25                  30

Leu Asn Asn Ser Lys Gly Glu Met Thr Asp Ala Ile Val Gly Phe Met
         35                  40                  45

Lys Leu Leu Leu Arg Leu Ala Arg Gln Lys Ser Asn Gln Val Ile Val
     50                  55                  60

Val Phe Asp Pro Pro Val Lys Thr Leu Arg His Glu Gln Tyr Glu Gly
 65                  70                  75                  80

Tyr Lys Ser Gly Arg Ala Gln Thr Pro Glu Asp Leu Arg Gly Gln Ile
                 85                  90                  95

Asn Arg Ile Arg Ala Leu Val Asp Ala Leu Gly Phe Pro Arg Leu Glu
             100                 105                 110

Glu Pro Gly Tyr Glu Ala Asp Asp Val Ile Ala Ser Leu Thr Arg Met
             115                 120                 125

Ala Glu Gly Lys Gly Tyr Glu Val Arg Ile Val Thr Ser Asp Arg Asp
         130                 135                 140

Ala Tyr Gln Leu Leu Asp Glu His Val Lys Val Ile Ala Asn Asp Phe
145                 150                 155                 160

Ser Leu Ile Gly Pro Ala Gln Val Glu Glu Lys Tyr Gly Val Thr Val
                 165                 170                 175

Arg Gln Trp Val Asp Tyr Arg Ala Leu Thr Gly Asp Ala Ser Asp Asn
             180                 185                 190

Ile Pro Gly Ala Lys Gly Ile Gly Pro Lys Thr Ala Ala Lys Leu Leu
             195                 200                 205

Gln Glu Tyr Gly Thr Leu Glu Lys Val Tyr Glu Ala Ala His Ala Gly
         210                 215                 220

Thr Leu Lys Pro Asp Gly Thr Arg Lys Lys Leu Leu Asp Ser Glu Glu
225                 230                 235                 240

Asn Val Lys Phe Ser His Asp Leu Ser Cys Met Val Thr Asp Leu Pro
                 245                 250                 255

Leu Asp Ile Glu Phe Gly Val Arg Arg Leu Pro Asp Asn Pro Leu Val
             260                 265                 270

Thr Glu Asp Leu Leu Thr Glu Leu Glu Leu His Ser Leu Arg Pro Met
         275                 280                 285

Ile Leu Gly Leu Asn Gly Pro Glu Gln Asp Gly His Ala Pro Asp Asp
290                 295                 300

Leu Leu Glu Arg Glu His Ala Gln Thr Pro Glu Glu Asp Glu Ala Ala
305                 310                 315                 320

Ala Leu Pro Ala Phe Ser Ala Pro Glu Leu Ala Glu Trp Gln Thr Pro
                 325                 330                 335

Ala Glu Gly Ala Val Trp Gly Tyr Val Leu Ser Arg Glu Asp Asp Leu
             340                 345                 350

Thr Ala Ala Leu Leu Ala Ala Thr Phe Glu Asp Gly Val Ala Arg
         355                 360                 365

Pro Ala Arg Val Ser Glu Pro Asp Glu Trp Ala Gln Ala Glu Ala Pro
370                 375                 380

Glu Asn Leu Phe Gly Glu Leu Leu Pro Ser Asp Lys Pro Leu Thr Lys
385                 390                 395                 400

Lys Glu Gln Lys Ala Leu Glu Lys Ala Gln Lys Asp Ala Glu Lys Ala
                 405                 410                 415

Arg Ala Lys Leu Arg Glu Gln Phe Pro Ala Thr Val Asp Glu Ala Glu
             420                 425                 430

Phe Val Gly Gln Arg Thr Val Thr Ala Ala Ala Ala Lys Ala Leu Ala
```

|     |     |     | 435 |     |     |     | 440 |     |     |     | 445 |     |
|-----|-----|-----|-----|-----|-----|-----|-----|-----|-----|-----|-----|-----|

Ala His Leu Ser Val Arg Gly Thr Val Val Glu Pro Gly Asp Pro
             450                 455                 460

Leu Leu Tyr Ala Tyr Leu Leu Asp Pro Ala Asn Thr Asn Met Pro Val
465                 470                 475                 480

Val Ala Lys Arg Tyr Leu Asp Arg Glu Trp Pro Ala Asp Ala Pro Thr
                 485                 490                 495

Arg Ala Ala Ile Thr Gly His Leu Val Arg Glu Leu Pro Pro Leu Leu
             500                 505                 510

Asp Asp Ala Arg Arg Lys Met Tyr Asp Glu Met Glu Lys Pro Leu Ser
             515                 520                 525

Gly Val Leu Gly Arg Met Glu Val Arg Gly Val Gln Val Asp Ser Asp
             530                 535                 540

Phe Leu Gln Thr Leu Ser Ile Gln Ala Gly Val Arg Leu Ala Asp Leu
545                 550                 555                 560

Glu Ser Gln Ile His Glu Tyr Ala Gly Glu Glu Phe His Ile Arg Ser
                 565                 570                 575

Pro Lys Gln Leu Glu Thr Val Leu Tyr Asp Lys Leu Glu Leu Ala Ser
             580                 585                 590

Ser Lys Lys Thr Lys Leu Thr Gly Gln Arg Ser Thr Ala Val Ser Ala
             595                 600                 605

Leu Glu Pro Leu Arg Asp Ala His Pro Ile Ile Pro Leu Val Leu Glu
610                 615                 620

Phe Arg Glu Leu Asp Lys Leu Arg Gly Thr Tyr Leu Asp Pro Ile Pro
625                 630                 635                 640

Asn Leu Val Asn Pro His Thr Gly Arg Leu His Thr Thr Phe Ala Gln
                 645                 650                 655

Thr Ala Val Ala Thr Gly Arg Leu Ser Ser Leu Asn Pro Asn Leu Gln
             660                 665                 670

Asn Ile Pro Ile Arg Ser Glu Leu Gly Arg Glu Ile Arg Lys Gly Phe
             675                 680                 685

Ile Ala Glu Asp Gly Phe Thr Leu Ile Ala Ala Asp Tyr Ser Gln Ile
             690                 695                 700

Glu Leu Arg Leu Leu Ala His Ile Ala Asp Asp Pro Leu Met Gln Gln
705                 710                 715                 720

Ala Phe Val Glu Gly Ala Asp Ile His Arg Arg Thr Ala Ala Gln Val
                 725                 730                 735

Leu Gly Leu Asp Glu Ala Thr Val Asp Ala Asn Gln Arg Arg Ala Ala
             740                 745                 750

Lys Thr Val Asn Phe Gly Val Leu Tyr Gly Met Ser Ala His Arg Leu
             755                 760                 765

Ser Asn Asp Leu Gly Ile Pro Tyr Ala Glu Ala Ala Thr Phe Ile Glu
             770                 775                 780

Ile Tyr Phe Ala Thr Tyr Pro Gly Ile Arg Arg Tyr Ile Asn His Thr
785                 790                 795                 800

Leu Asp Phe Gly Arg Thr His Gly Tyr Val Glu Thr Leu Tyr Gly Arg
                 805                 810                 815

Arg Arg Tyr Val Pro Gly Leu Ser Ser Arg Asn Arg Val Gln Arg Glu
             820                 825                 830

Ala Glu Glu Arg Leu Ala Tyr Asn Met Pro Ile Gln Gly Thr Ala Ala
             835                 840                 845

Asp Ile Met Lys Leu Ala Met Val Gln Leu Asp Pro Gln Leu Asp Ala
             850                 855                 860

-continued

```
Ile Gly Ala Arg Met Leu Leu Gln Val His Asp Glu Leu Ile Glu
865                 870                 875                 880

Ala Pro Leu Asp Lys Ala Glu Gln Val Ala Ala Leu Thr Lys Lys Val
            885                 890                 895

Met Glu Asn Val Val Gln Leu Lys Val Pro Leu Ala Val Glu Val Gly
            900                 905                 910

Thr Gly Pro Asn Trp Phe Asp Thr Lys
        915                 920

<210> SEQ ID NO 37
<211> LENGTH: 892
<212> TYPE: PRT
<213> ORGANISM: Thermosipho africanus
<220> FEATURE:
<223> OTHER INFORMATION: Thermosipho africanus DNA polymerase (Taf)

<400> SEQUENCE: 37

Met Gly Lys Met Phe Leu Phe Asp Gly Thr Gly Leu Val Tyr Arg Ala
1               5                   10                  15

Phe Tyr Ala Ile Asp Gln Ser Leu Gln Thr Ser Ser Gly Leu His Thr
            20                  25                  30

Asn Ala Val Tyr Gly Leu Thr Lys Met Leu Ile Lys Phe Leu Lys Glu
        35                  40                  45

His Ile Ser Ile Gly Lys Asp Ala Cys Val Phe Val Leu Asp Ser Lys
    50                  55                  60

Gly Gly Ser Lys Lys Arg Lys Asp Ile Leu Glu Thr Tyr Lys Ala Asn
65                  70                  75                  80

Arg Pro Ser Thr Pro Asp Leu Leu Leu Glu Gln Ile Pro Tyr Val Glu
                85                  90                  95

Glu Leu Val Asp Ala Leu Gly Ile Lys Val Leu Lys Ile Glu Gly Phe
            100                 105                 110

Glu Ala Asp Asp Ile Ile Ala Thr Leu Ser Lys Lys Phe Glu Ser Asp
        115                 120                 125

Phe Glu Lys Val Asn Ile Ile Thr Gly Asp Lys Asp Leu Leu Gln Leu
    130                 135                 140

Val Ser Asp Lys Val Phe Val Trp Arg Val Glu Arg Gly Ile Thr Asp
145                 150                 155                 160

Leu Val Leu Tyr Asp Arg Asn Lys Val Ile Glu Lys Tyr Gly Ile Tyr
                165                 170                 175

Pro Glu Gln Phe Lys Asp Tyr Leu Ser Leu Val Gly Asp Gln Ile Asp
            180                 185                 190

Asn Ile Pro Gly Val Lys Gly Ile Gly Lys Lys Thr Ala Val Ser Leu
        195                 200                 205

Leu Lys Lys Tyr Asn Ser Leu Glu Asn Val Leu Lys Asn Ile Asn Leu
    210                 215                 220

Leu Thr Glu Lys Leu Arg Arg Leu Leu Glu Asp Ser Lys Glu Asp Leu
225                 230                 235                 240

Gln Lys Ser Ile Glu Leu Val Glu Leu Ile Tyr Asp Val Pro Met Asp
                245                 250                 255

Val Glu Lys Asp Glu Ile Ile Tyr Arg Gly Tyr Asn Pro Asp Lys Leu
            260                 265                 270

Leu Lys Val Leu Lys Lys Tyr Glu Phe Ser Ser Ile Ile Lys Glu Leu
        275                 280                 285

Asn Leu Gln Glu Lys Leu Glu Lys Glu Tyr Ile Leu Val Asp Asn Glu
    290                 295                 300
```

-continued

```
Asp Lys Leu Lys Lys Leu Ala Glu Glu Ile Glu Lys Tyr Lys Thr Phe
305                 310                 315                 320

Ser Ile Asp Thr Glu Thr Thr Ser Leu Asp Pro Phe Glu Ala Lys Leu
            325                 330                 335

Val Gly Ile Ser Ile Ser Thr Met Glu Gly Lys Ala Tyr Tyr Ile Pro
                340                 345                 350

Val Ser His Phe Gly Ala Lys Asn Ile Ser Lys Ser Leu Ile Asp Lys
                355                 360                 365

Phe Leu Lys Gln Ile Leu Gln Glu Lys Asp Tyr Asn Ile Val Gly Gln
370                 375                 380

Asn Leu Lys Phe Asp Tyr Glu Ile Phe Lys Ser Met Gly Phe Ser Pro
385                 390                 395                 400

Asn Val Pro His Phe Asp Thr Met Ile Ala Ala Tyr Leu Leu Asn Pro
                405                 410                 415

Asp Glu Lys Arg Phe Asn Leu Glu Glu Leu Ser Leu Lys Tyr Leu Gly
                420                 425                 430

Tyr Lys Met Ile Ser Phe Asp Glu Leu Val Asn Glu Asn Val Pro Leu
                435                 440                 445

Phe Gly Asn Asp Phe Ser Tyr Val Pro Leu Glu Arg Ala Val Glu Tyr
450                 455                 460

Ser Cys Glu Asp Ala Asp Val Thr Tyr Arg Ile Phe Arg Lys Leu Gly
465                 470                 475                 480

Arg Lys Ile Tyr Glu Asn Glu Met Glu Lys Leu Phe Tyr Glu Ile Glu
                485                 490                 495

Met Pro Leu Ile Asp Val Leu Ser Glu Met Glu Leu Asn Gly Val Tyr
                500                 505                 510

Phe Asp Glu Glu Tyr Leu Lys Glu Leu Ser Lys Lys Tyr Gln Glu Lys
                515                 520                 525

Met Asp Gly Ile Lys Glu Lys Val Phe Glu Ile Ala Gly Glu Thr Phe
                530                 535                 540

Asn Leu Asn Ser Ser Thr Gln Val Ala Tyr Ile Leu Phe Glu Lys Leu
545                 550                 555                 560

Asn Ile Ala Pro Tyr Lys Lys Thr Ala Thr Gly Lys Phe Ser Thr Asn
                565                 570                 575

Ala Glu Val Leu Glu Glu Leu Ser Lys Glu His Glu Ile Ala Lys Leu
                580                 585                 590

Leu Leu Glu Tyr Arg Lys Tyr Gln Lys Leu Lys Ser Thr Tyr Ile Asp
                595                 600                 605

Ser Ile Pro Leu Ser Ile Asn Arg Lys Thr Asn Arg Val His Thr Thr
610                 615                 620

Phe His Gln Thr Gly Thr Ser Thr Gly Arg Leu Ser Ser Ser Asn Pro
625                 630                 635                 640

Asn Leu Gln Asn Leu Pro Thr Arg Ser Glu Glu Gly Lys Glu Ile Arg
                645                 650                 655

Lys Ala Val Arg Pro Gln Arg Gln Asp Trp Trp Ile Leu Gly Ala Asp
                660                 665                 670

Tyr Ser Gln Ile Glu Leu Arg Val Leu Ala His Val Ser Lys Asp Glu
                675                 680                 685

Asn Leu Leu Lys Ala Phe Lys Glu Asp Leu Asp Ile His Thr Ile Thr
                690                 695                 700

Ala Ala Lys Ile Phe Gly Val Ser Glu Met Phe Val Ser Glu Gln Met
705                 710                 715                 720
```

Arg Arg Val Gly Lys Met Val Asn Phe Ala Ile Ile Tyr Gly Val Ser
            725                 730                 735
Pro Tyr Gly Leu Ser Lys Arg Ile Gly Leu Ser Val Ser Glu Thr Lys
            740                 745                 750
Lys Ile Ile Asp Asn Tyr Phe Arg Tyr Tyr Lys Gly Val Phe Glu Tyr
            755                 760                 765
Leu Lys Arg Met Lys Asp Glu Ala Arg Lys Gly Tyr Val Thr Thr
            770                 775                 780
Leu Phe Gly Arg Arg Tyr Ile Pro Gln Leu Arg Ser Lys Asn Gly
785                 790                 795                 800
Asn Arg Val Gln Glu Gly Glu Arg Ile Ala Val Asn Thr Pro Ile Gln
            805                 810                 815
Gly Thr Ala Ala Asp Ile Ile Lys Ile Ala Met Ile Asn Ile His Asn
            820                 825                 830
Arg Leu Lys Lys Glu Asn Leu Arg Ser Lys Met Ile Leu Gln Val His
            835                 840                 845
Asp Glu Leu Val Phe Glu Val Pro Asp Asn Glu Leu Glu Ile Val Lys
            850                 855                 860
Asp Leu Val Arg Asp Glu Met Glu Asn Ala Val Lys Leu Asp Val Pro
865                 870                 875                 880
Leu Lys Val Asp Val Tyr Tyr Gly Lys Glu Trp Glu
            885                 890

<210> SEQ ID NO 38
<211> LENGTH: 893
<212> TYPE: PRT
<213> ORGANISM: Thermotoga maritima
<220> FEATURE:
<223> OTHER INFORMATION: Thermotoga maritima DNA polymerase (Tma)

<400> SEQUENCE: 38

Met Ala Arg Leu Phe Leu Phe Asp Gly Thr Ala Leu Ala Tyr Arg Ala
1               5                   10                  15
Tyr Tyr Ala Leu Asp Arg Ser Leu Ser Thr Ser Thr Gly Ile Pro Thr
            20                  25                  30
Asn Ala Thr Tyr Gly Val Ala Arg Met Leu Val Arg Phe Ile Lys Asp
            35                  40                  45
His Ile Ile Val Gly Lys Asp Tyr Val Ala Val Ala Phe Asp Lys Lys
        50                  55                  60
Ala Ala Thr Phe Arg His Lys Leu Leu Glu Thr Tyr Lys Ala Gln Arg
65              70                  75                  80
Pro Lys Thr Pro Asp Leu Leu Ile Gln Gln Leu Pro Tyr Ile Lys Lys
            85                  90                  95
Leu Val Glu Ala Leu Gly Met Lys Val Leu Glu Val Glu Gly Tyr Glu
            100                 105                 110
Ala Asp Asp Ile Ile Ala Thr Leu Ala Val Lys Gly Leu Pro Leu Phe
            115                 120                 125
Asp Glu Ile Phe Ile Val Thr Gly Asp Lys Asp Met Leu Gln Leu Val
            130                 135                 140
Asn Glu Lys Ile Lys Val Trp Arg Ile Val Lys Gly Ile Ser Asp Leu
145                 150                 155                 160
Glu Leu Tyr Asp Ala Gln Lys Val Lys Glu Lys Tyr Gly Val Glu Pro
                165                 170                 175
Gln Gln Ile Pro Asp Leu Leu Ala Leu Thr Gly Asp Glu Ile Asp Asn
            180                 185                 190

```
Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
                260                 265                 270

Pro Leu Leu Lys Glu Leu Glu Phe Ala Ser Ile Met Lys Glu Leu Gln
    275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
        515                 520                 525

Leu Glu Glu Leu Ala Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
```

```
                   610                 615                 620
Ser Phe Asn Gln Thr Gly Thr Ala Thr Gly Arg Leu Ser Ser Asp
625                 630                 635                 640

Pro Asn Leu Gln Asn Leu Pro Thr Lys Ser Glu Gly Lys Glu Ile
                    645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
                675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                    725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
                755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                    805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                    885                 890

<210> SEQ ID NO 39
<211> LENGTH: 893
<212> TYPE: PRT
<213> ORGANISM: Thermotoga neopolitana
<220> FEATURE:
<223> OTHER INFORMATION: Thermotoga neopolitana DNA polymerase (Tne)

<400> SEQUENCE: 39

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
```

```
                         85                   90                    95
Leu Ile Glu Ala Leu Gly Phe Lys Val Leu Glu Leu Glu Gly Tyr Glu
                100                 105                 110

Ala Asp Asp Ile Ile Ala Thr Leu Ala Val Arg Ala Arg Phe Leu
            115                 120                 125

Met Arg Phe Ser Leu Ile Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Glu Arg Tyr Gly Val Glu Pro
                165                 170                 175

His Gln Ile Pro Asp Leu Leu Ala Leu Thr Gly Asp Asp Ile Asp Asn
                180                 185                 190

Ile Pro Gly Val Thr Gly Ile Gly Glu Lys Thr Ala Val Gln Leu Leu
            195                 200                 205

Gly Lys Tyr Arg Asn Leu Glu Tyr Ile Leu Glu His Ala Arg Glu Leu
    210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
    275                 280                 285

Leu Tyr Glu Glu Ala Glu Pro Thr Gly Tyr Glu Ile Val Lys Asp His
290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
                325                 330                 335

Val Gly Ile Ser Val Ser Phe Lys Pro Lys Thr Ala Tyr Tyr Ile Pro
            340                 345                 350

Leu His His Arg Asn Ala His Asn Leu Asp Glu Thr Leu Val Leu Ser
    355                 360                 365

Lys Leu Lys Glu Ile Leu Glu Asp Pro Ser Ser Lys Ile Val Gly Gln
    370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                405                 410                 415

Asn Glu Lys Lys Phe Asn Leu Glu Asp Leu Ser Leu Lys Phe Leu Gly
                420                 425                 430

Tyr Lys Met Thr Ser Tyr Gln Glu Leu Met Ser Phe Ser Ser Pro Leu
    435                 440                 445

Phe Gly Phe Ser Phe Ala Asp Val Pro Val Asp Lys Ala Ala Glu Tyr
    450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
                485                 490                 495

Met Pro Leu Val Asn Val Leu Ala Arg Met Glu Phe Asn Trp Val Tyr
            500                 505                 510
```

Val Asp Thr Glu Phe Leu Lys Lys Leu Ser Glu Glu Tyr Gly Lys Lys
            515                 520                 525

Leu Glu Glu Leu Ala Glu Lys Ile Tyr Gln Ile Ala Gly Glu Pro Phe
530                 535                 540

Asn Ile Asn Ser Pro Lys Gln Val Ser Asn Ile Leu Phe Glu Lys Leu
545                 550                 555                 560

Gly Ile Lys Pro Arg Gly Lys Thr Thr Lys Thr Gly Asp Tyr Ser Thr
            565                 570                 575

Arg Ile Glu Val Leu Glu Glu Ile Ala Asn Glu His Glu Ile Val Pro
            580                 585                 590

Leu Ile Leu Glu Phe Arg Lys Ile Leu Lys Leu Lys Ser Thr Tyr Ile
            595                 600                 605

Asp Thr Leu Pro Lys Leu Val Asn Pro Lys Thr Gly Arg Phe His Ala
            610                 615                 620

Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asp Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Val Lys Ala Phe Glu Glu Gly Ile Asp Val His Thr Leu
            690                 695                 700

Thr Ala Ser Arg Ile Tyr Asn Val Lys Pro Glu Val Asn Glu Glu
705                 710                 715                 720

Met Arg Arg Val Gly Lys Met Val Asn Phe Ser Ile Ile Tyr Gly Val
            725                 730                 735

Thr Pro Tyr Gly Leu Ser Val Arg Leu Gly Ile Pro Val Lys Glu Ala
            740                 745                 750

Glu Lys Met Ile Ile Ser Tyr Phe Thr Leu Tyr Pro Lys Val Arg Ser
            755                 760                 765

Tyr Ile Gln Gln Val Val Ala Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Lys Asn Thr Gln Ser Glu Gly Glu Arg Ile Ala Ile Asn Thr Pro Ile
            805                 810                 815

Gln Gly Thr Ala Ala Asp Ile Ile Lys Leu Ala Met Ile Asp Ile Asp
            820                 825                 830

Glu Glu Leu Arg Lys Arg Asn Met Lys Ser Arg Met Ile Ile Gln Val
            835                 840                 845

His Asp Glu Leu Val Phe Glu Val Pro Asp Glu Glu Lys Glu Glu Leu
            850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
            885                 890

<210> SEQ ID NO 40
<211> LENGTH: 876
<212> TYPE: PRT
<213> ORGANISM: Bacillus stearothermophilus
<220> FEATURE:

<223> OTHER INFORMATION: Bacillus stearothermophilus DNA polymerase (Bst)

<400> SEQUENCE: 40

```
Met Lys Asn Lys Leu Val Leu Ile Asp Gly Asn Ser Val Ala Tyr Arg
 1               5                  10                  15

Ala Phe Phe Ala Leu Pro Leu Leu His Asn Asp Lys Gly Ile His Thr
             20                  25                  30

Asn Ala Val Tyr Gly Phe Thr Met Met Leu Asn Lys Ile Leu Ala Glu
         35                  40                  45

Glu Gln Pro Thr His Ile Leu Val Ala Phe Asp Ala Gly Lys Thr Thr
     50                  55                  60

Phe Arg His Glu Thr Phe Gln Asp Tyr Lys Gly Arg Gln Gln Thr
 65                  70                  75                  80

Pro Pro Glu Leu Ser Glu Gln Phe Pro Leu Leu Arg Glu Leu Leu Lys
                 85                  90                  95

Ala Tyr Arg Ile Pro Ala Tyr Glu Leu Asp His Tyr Glu Ala Asp Asp
            100                 105                 110

Ile Ile Gly Thr Met Ala Ala Arg Ala Glu Arg Glu Gly Phe Ala Val
        115                 120                 125

Lys Val Ile Ser Gly Asp Arg Asp Leu Thr Gln Leu Ala Ser Pro Gln
130                 135                 140

Val Thr Val Glu Ile Thr Lys Lys Gly Ile Thr Asp Ile Glu Ser Tyr
145                 150                 155                 160

Thr Pro Glu Thr Val Val Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Lys Gln Phe
        195                 200                 205

Gly Thr Val Glu Asn Val Leu Ala Ser Ile Asp Glu Ile Lys Gly Glu
    210                 215                 220

Lys Leu Lys Glu Asn Leu Arg Gln Tyr Arg Asp Leu Ala Leu Leu Ser
225                 230                 235                 240

Lys Gln Leu Ala Ala Ile Cys Arg Asp Ala Pro Val Glu Leu Thr Leu
                245                 250                 255

Asp Asp Ile Val Tyr Lys Gly Asp Arg Glu Lys Val Val Ala Leu
            260                 265                 270

Phe Gln Glu Leu Gly Phe Gln Ser Phe Leu Asp Lys Met Ala Val Gln
        275                 280                 285

Thr Asp Glu Gly Glu Lys Pro Leu Ala Gly Met Asp Phe Ala Ile Ala
    290                 295                 300

Asp Ser Val Thr Asp Glu Met Leu Ala Asp Lys Ala Ala Leu Val Val
305                 310                 315                 320

Glu Val Val Gly Asp Asn Tyr His His Ala Pro Ile Val Gly Ile Ala
                325                 330                 335

Leu Ala Asn Glu Arg Gly Arg Phe Phe Leu Arg Pro Glu Thr Ala Leu
            340                 345                 350

Ala Asp Pro Lys Phe Leu Ala Trp Leu Gly Asp Glu Thr Lys Lys Lys
        355                 360                 365

Thr Met Phe Asp Ser Lys Arg Ala Ala Val Ala Leu Lys Trp Lys Gly
    370                 375                 380

Ile Glu Leu Arg Gly Val Val Phe Asp Leu Leu Leu Ala Ala Tyr Leu
385                 390                 395                 400
```

```
Leu Asp Pro Ala Gln Ala Ala Gly Asp Val Ala Ala Val Ala Lys Met
                405                 410                 415

His Gln Tyr Glu Ala Val Arg Ser Asp Glu Ala Val Tyr Gly Lys Gly
                420                 425                 430

Ala Lys Arg Thr Val Pro Asp Glu Pro Thr Leu Ala Glu His Leu Ala
                435                 440                 445

Arg Lys Ala Ala Ala Ile Trp Ala Leu Glu Glu Pro Leu Met Asp Glu
                450                 455                 460

Leu Arg Arg Asn Glu Gln Asp Arg Leu Leu Thr Glu Leu Glu Gln Pro
465                 470                 475                 480

Leu Ala Gly Ile Leu Ala Asn Met Glu Phe Thr Gly Val Lys Val Asp
                485                 490                 495

Thr Lys Arg Leu Glu Gln Met Gly Ala Glu Leu Thr Glu Gln Leu Gln
                500                 505                 510

Ala Val Glu Arg Arg Ile Tyr Glu Leu Ala Gly Gln Glu Phe Asn Ile
                515                 520                 525

Asn Ser Pro Lys Gln Leu Gly Thr Val Leu Phe Asp Lys Leu Gln Leu
                530                 535                 540

Pro Val Leu Lys Lys Thr Lys Thr Gly Tyr Ser Thr Ser Ala Asp Val
545                 550                 555                 560

Leu Glu Lys Leu Ala Pro His His Glu Ile Val Glu His Ile Leu His
                565                 570                 575

Tyr Arg Gln Leu Gly Lys Leu Gln Ser Thr Tyr Ile Glu Gly Leu Leu
                580                 585                 590

Lys Val Val His Pro Val Thr Gly Lys Val His Thr Met Phe Asn Gln
                595                 600                 605

Ala Leu Thr Gln Thr Gly Arg Leu Ser Ser Val Glu Pro Asn Leu Gln
610                 615                 620

Asn Ile Pro Ile Arg Leu Glu Glu Gly Arg Lys Ile Arg Gln Ala Phe
625                 630                 635                 640

Val Pro Ser Glu Pro Asp Trp Leu Ile Phe Ala Ala Asp Tyr Ser Gln
                645                 650                 655

Ile Glu Leu Arg Val Leu Ala His Ile Ala Glu Asp Asp Asn Leu Ile
                660                 665                 670

Glu Ala Phe Arg Arg Gly Leu Asp Ile His Thr Lys Thr Ala Met Asp
                675                 680                 685

Ile Phe His Val Ser Glu Glu Asp Val Thr Ala Asn Met Arg Arg Gln
                690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Thr Arg Lys Glu Ala Ala Glu Phe Ile
                725                 730                 735

Glu Arg Tyr Phe Ala Ser Phe Pro Gly Val Lys Gln Tyr Met Asp Asn
                740                 745                 750

Ile Val Gln Glu Ala Lys Gln Lys Gly Tyr Val Thr Thr Leu Leu His
                755                 760                 765

Arg Arg Arg Tyr Leu Pro Asp Ile Thr Ser Arg Asn Phe Asn Val Arg
                770                 775                 780

Ser Phe Ala Glu Arg Thr Ala Met Asn Thr Pro Ile Gln Gly Ser Ala
785                 790                 795                 800

Ala Asp Ile Ile Lys Lys Ala Met Ile Asp Leu Ser Val Arg Leu Arg
                805                 810                 815
```

-continued

```
Glu Glu Arg Leu Gln Ala Arg Leu Leu Leu Gln Val His Asp Glu Leu
            820                 825                 830

Ile Leu Glu Ala Pro Lys Glu Glu Ile Glu Arg Leu Cys Arg Leu Val
            835                 840                 845

Pro Glu Val Met Glu Gln Ala Val Ala Leu Arg Val Pro Leu Lys Val
            850                 855                 860

Asp Tyr His Tyr Gly Pro Thr Trp Tyr Asp Ala Lys
865                 870                 875

<210> SEQ ID NO 41
<211> LENGTH: 877
<212> TYPE: PRT
<213> ORGANISM: Bacillus caldotenax
<220> FEATURE:
<223> OTHER INFORMATION: Bacillus caldotenax DNA polymerase (Bca)

<400> SEQUENCE: 41

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
        50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
        130                 135                 140

Val Thr Val Asp Ile Thr Lys Lys Gly Ile Thr Asp Ile Glu Pro Tyr
145                 150                 155                 160

Thr Pro Glu Ala Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
            195                 200                 205

Gly Thr Val Glu Asn Val Leu Ala Ser Ile Asp Glu Ile Lys Gly Glu
        210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300
```

```
Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Lys Met
        405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ala Ile Trp Ala Leu Glu Arg Pro Phe Leu Asp Glu
450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Glu Glu Leu Ala Glu Gln Leu Arg
        500                 505                 510

Thr Val Glu Gln Arg Ile Tyr Glu Leu Ala Gly Gln Glu Phe Asn Ile
    515                 520                 525

Asn Ser Pro Lys Gln Leu Gly Val Ile Leu Phe Glu Lys Leu Gln Leu
530                 535                 540

Pro Val Leu Lys Lys Ser Lys Thr Gly Tyr Ser Thr Ser Ala Asp Val
545                 550                 555                 560

Leu Glu Lys Leu Ala Pro Tyr His Glu Ile Val Glu Asn Ile Leu Gln
                565                 570                 575

His Tyr Arg Gln Leu Gly Lys Leu Gln Ser Thr Tyr Ile Glu Gly Leu
        580                 585                 590

Leu Lys Val Val Arg Pro Asp Thr Lys Lys Val His Thr Ile Phe Asn
    595                 600                 605

Gln Ala Leu Thr Gln Thr Gly Arg Leu Ser Ser Thr Glu Pro Asn Leu
610                 615                 620

Gln Asn Ile Pro Ile Arg Leu Glu Glu Gly Arg Lys Ile Arg Gln Ala
625                 630                 635                 640

Phe Val Pro Ser Glu Ser Asp Trp Leu Ile Phe Ala Ala Asp Tyr Ser
                645                 650                 655

Gln Ile Glu Leu Arg Val Leu Ala His Ile Ala Glu Asp Asp Asn Leu
        660                 665                 670

Met Glu Ala Phe Arg Arg Asp Leu Asp Ile His Thr Lys Thr Ala Met
    675                 680                 685

Asp Ile Phe Gln Val Ser Glu Asp Glu Val Thr Pro Asn Met Arg Arg
690                 695                 700

Gln Ala Lys Ala Val Asn Phe Gly Ile Val Tyr Gly Ile Ser Asp Tyr
705                 710                 715                 720

Gly Leu Ala Gln Asn Leu Asn Ile Ser Arg Lys Glu Ala Ala Glu Phe
```

```
                         725                 730                 735
Ile Glu Arg Tyr Phe Glu Ser Phe Pro Gly Val Lys Arg Tyr Met Glu
            740                 745                 750

Asn Ile Val Gln Glu Ala Lys Gln Lys Gly Tyr Val Thr Thr Leu Leu
            755                 760                 765

His Arg Arg Arg Tyr Leu Pro Asp Ile Thr Ser Arg Asn Phe Asn Val
            770                 775                 780

Arg Ser Phe Ala Glu Arg Met Ala Met Asn Thr Pro Ile Gln Gly Ser
785                 790                 795                 800

Ala Ala Asp Ile Ile Lys Lys Ala Met Ile Asp Leu Asn Ala Arg Leu
                805                 810                 815

Lys Glu Glu Arg Leu Gln Ala Arg Leu Leu Leu Gln Val His Asp Glu
            820                 825                 830

Leu Ile Leu Glu Ala Pro Lys Glu Glu Met Glu Arg Leu Cys Arg Leu
            835                 840                 845

Val Pro Glu Val Met Glu Gln Ala Val Thr Leu Arg Val Pro Leu Lys
            850                 855                 860

Val Asp Tyr His Tyr Gly Ser Thr Trp Tyr Asp Ala Lys
865                 870                 875

<210> SEQ ID NO 42
<211> LENGTH: 14
<212> TYPE: PRT
<213> ORGANISM: Artificial Sequence
<220> FEATURE:
<223> OTHER INFORMATION: synthetic DNA polymerase domain motif
<220> FEATURE:
<221> NAME/KEY: VARIANT
<222> LOCATION: (4)...(4)
<223> OTHER INFORMATION: Xaa = Glu, Arg or Thr
<220> FEATURE:
<221> NAME/KEY: VARIANT
<222> LOCATION: (7)...(7)
<223> OTHER INFORMATION: Xaa = Phe, Tyr or Leu
<220> FEATURE:
<221> NAME/KEY: VARIANT
<222> LOCATION: (8)...(8)
<223> OTHER INFORMATION: Xaa = Gly or His
<220> FEATURE:
<221> NAME/KEY: VARIANT
<222> LOCATION: (10)...(10)
<223> OTHER INFORMATION: Xaa = Arg or Lys
<220> FEATURE:
<221> NAME/KEY: VARIANT
<222> LOCATION: (11)...(11)
<223> OTHER INFORMATION: Xaa = Gly, Ala, Leu, Met, Trp, Pro, Ser, Thr,
      Phe, Tyr, Cys, Asn, Gln, Asp, Glu, Lys, Val, Ile or His
<220> FEATURE:
<221> NAME/KEY: VARIANT
<222> LOCATION: (12)...(12)
<223> OTHER INFORMATION: Xaa = Tyr or Asp
<220> FEATURE:
<221> NAME/KEY: VARIANT
<222> LOCATION: (13)...(13)
<223> OTHER INFORMATION: Xaa = Val, Ile or Leu

<400> SEQUENCE: 42

Gly Tyr Val Xaa Thr Leu Xaa Xaa Arg Xaa Xaa Xaa Xaa Pro
1               5                   10
```